US010266845B2

(12) United States Patent
Cronin et al.

(10) Patent No.: US 10,266,845 B2
(45) Date of Patent: Apr. 23, 2019

(54) ENHANCED AAV-MEDIATED GENE TRANSFER FOR RETINAL THERAPIES

(71) Applicant: The Trustees of the University of Pennsylvania, Philadelphia, PA (US)

(72) Inventors: Therese Cronin, Basel (CH); Jean Bennett, Bryn Mawr, PA (US); Luk E. Vandenberghe, Weston, MA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 19 days.

(21) Appl. No.: 15/246,001

(22) Filed: Aug. 24, 2016

(65) Prior Publication Data

US 2017/0049910 A1 Feb. 23, 2017

Related U.S. Application Data

(62) Division of application No. 14/766,172, filed as application No. PCT/US2014/015340 on Feb. 7, 2014, now Pat. No. 9,567,376.

(60) Provisional application No. 61/762,775, filed on Feb. 8, 2013.

(51) Int. Cl.
| | |
|---|---|
| *C12N 15/86* | (2006.01) |
| *C07K 14/015* | (2006.01) |
| *A61K 48/00* | (2006.01) |
| *C07K 14/005* | (2006.01) |
| *C12N 7/00* | (2006.01) |
| *A61K 38/17* | (2006.01) |
| *C12N 15/864* | (2006.01) |
| *C07K 14/72* | (2006.01) |

(52) U.S. Cl.
CPC ............ *C12N 15/86* (2013.01); *A61K 38/177* (2013.01); *A61K 48/0058* (2013.01); *A61K 48/0075* (2013.01); *C07K 14/005* (2013.01); *C07K 14/015* (2013.01); *C07K 14/723* (2013.01); *C12N 7/00* (2013.01); *C12N 15/8645* (2013.01); *C12N 2750/14121* (2013.01); *C12N 2750/14122* (2013.01); *C12N 2750/14143* (2013.01); *C12N 2830/008* (2013.01)

(58) Field of Classification Search
CPC ...... C07K 14/005; C07K 14/705; C07K 7/06; C07K 14/015; A61K 48/00; A61K 38/177; A61K 48/0008; A61K 48/0075; C12N 15/86; C12N 2750/14122; C12N 2830/008; C12N 7/00; C12N 2750/14121; C12N 2750/14151; C12N 15/8645; C12N 2750/14143
See application file for complete search history.

(56) References Cited

U.S. PATENT DOCUMENTS

| | | | |
|---|---|---|---|
| 9,193,956 B2* | 11/2015 | Schaffer | C12N 7/00 |
| 9,493,788 B2* | 11/2016 | Gao | C07K 14/755 |
| 2003/0228282 A1 | 12/2003 | Guo et al. | |
| 2004/0052764 A1 | 3/2004 | Hildinger et al. | |
| 2012/0066783 A1 | 3/2012 | Kay et al. | |

FOREIGN PATENT DOCUMENTS

| | | |
|---|---|---|
| WO | WO 2010/011404 | 1/2010 |
| WO | WO 2012/051599 | 4/2012 |
| WO | 2012/145601 A2 | 10/2012 |
| WO | WO-2012/145601 A2 | 10/2012 |

OTHER PUBLICATIONS

Stieger et al. Molecular Ther 2008;16:916-23.*
Raupp et al., "The threefold protrusions of adeno-associated virus type 8 are involved in cell surface targeting as well as postattachment processing", J. Virol., vol. 86(17):9396-9408, Jun. 20, 2012.
International Search Report, dated Apr. 16, 2014, issued in corresponding International Patent Application No. PCT/US2014/015340.
Asokan et al, Reengineering a receptor footprint of adeno-associated virus enables selective and systemic gene transfer to muscle, Nature Biotechnology, 28(1):79-82 (Jan. 2010).
Xuan et al, Characterization of the relationship o9f AAV capsid domain swapping to liver transduction efficiency, Molecular Therapy, 5(11):1955-62 (Nov. 2007).
Cronin et al, Efficient transduction and optogenic stimulation of retinal bipolar cells by a synthetic adeno-associated virus capsid and promoter, EMBO Molecular Medicine, 6:1175-1190 (Aug. 2014).
European Search Report dated Aug. 17, 2016 issued in corresponding EP application No. 14749120.3.
Date of Search Report Apr. 16, 2014, WO, PCT/US2014/015340.
Raupp, J Virol, The threefold protrusions of adeno-associated virus type 8 are involved in cell surface targeting as well as postattachment processing, vol. 86(17):9696-9408, Jun. 20, 2012.

* cited by examiner

Primary Examiner — Kevin K Hill
(74) Attorney, Agent, or Firm — Howson & Howson LLP; Colleen M. Schaller

(57) ABSTRACT

Described herein are capsid proteins and adeno-associated viruses capable of targeting various types of ocular cells including bipolar and horizontal cells. Also described herein are methods of treating various ocular disorders in a subject in need thereof by administering to the subject an effective concentration of a composition comprising the recombinant adeno-associated virus (AAV) of the invention.

9 Claims, 13 Drawing Sheets
Specification includes a Sequence Listing.

FIGURE 1

AAV1_VP1- SEQ ID NO: 21
AAV2_VP1- SEQ ID NO: 22
AAV3_VP1- SEQ ID NO: 23
AAV3B_VP1- SEQ ID NO: 24
AAV4_VP1- SEQ ID NO: 25
AAV6_VP1- SEQ ID NO: 26
AAV7_VP1- SEQ ID NO: 27
AAV8_VP1- SEQ ID NO: 8

FIGURE 5

(from aa585)

| | | | | | | | | | | |
|---|---|---|---|---|---|---|---|---|---|---|
| WT | CAG | CAG | CAA | AAC | ACG | GCT | CCT | CAA | ATT | -SEQ ID NO: 11 |
| | Gln | Gln | Gln | Asn | Thr | Ala | Pro | Gln | Ile | -SEQ ID NO: 12 |
| | *P* | *P* | *P* | *P* | *(P)* | *(N)* | *P^* | *P* | *(N)\** | |
| | | | | | | | | | | |
| Var 1 | TAT | CTT | ATG | CGT | TAT | ATT | GGT | GTT | TTT | -SEQ ID NO: 13 |
| | Tyr | Leu | Met | Arg | Tyr | Ile | Gly | Gly | Phe | -SEQ ID NO: 14 |
| | *P* | *N\** | *N\** | *B^* | *P* | *(N)\** | *N* | *N* | *N\** | |
| | | | | | | | | | | |
| Var 2 | CCT | GAG | CGG | ACG | GCG | ATG | AGT | CTT | CCG | -SEQ ID NO: 9 |
| | Pro | Glu | Arg | Thr | Ala | Met | Ser | Leu | Pro | -SEQ ID NO: 1 |
| | *P^* | *A* | *B^* | *N* | *N* | *N\** | *P* | *N \** | *P^* | |
| | | | | | | | | | | |
| Var 3 | AGT | TTT | AGT | CGT | GCG | GTT | CTT | TGT | GAT | -SEQ ID NO: 10 |
| | Ser | Phe | Ser | Arg | Ala | Val | Leu | Cys | Asp | -SEQ ID NO: 2 |
| | *P* | *N\** | *P* | *B^* | *N* | *N \** | *N \** | *P* | *A* | |
| | | | | | | | | | | |
| Var 4 | CAT | TGT | GTG | GAT | TGT | TGT | GCG | TCT | TAT | -SEQ ID NO: 15 |
| | His | Cys | Val | Asp | Cys | Cys | Ala | Ser | Tyr | -SEQ ID NO: 16 |
| | *B^* | *P* | *N\** | *A* | *P* | *P* | *N* | *P* | *P* | |
| | | | | | | | | | | |
| Var 5 | CAT | ACT | GAG | TAT | ATG | AGT | GAG | TAG | CTC | -SEQ ID NO: 17 |
| | His | Thr | Glu | Tyr | Met | Ser | Glu | !!!! | Leu | -SEQ ID NO: 18 |
| | *B^* | *N* | *A* | *P* | *N\** | *P* | *A* | *stop* | *N \** | |
| | | | | | | | | | | |
| Var 6 | CCG | ATT | TTT | GTT | GGG | TGT | TCT | GTG | CTT | -SEQ ID NO: 19 |
| | Pro | Ile | Phe | Val | Gly | Cys | Ser | Val | Leu | -SEQ ID NO: 20 |
| | *P^* | *(N)\** | *N\** | *N\** | *N* | *P* | *P* | *N\** | *N\** | |

POS: Photoreceptor Outer Segments; ONL: Outer Nuclear Layer; OPL: Outer Plexiform Layer; IPL: Inner Plexiform Layer; GCL: Ganglion Cell Layer.

FIGURE 7
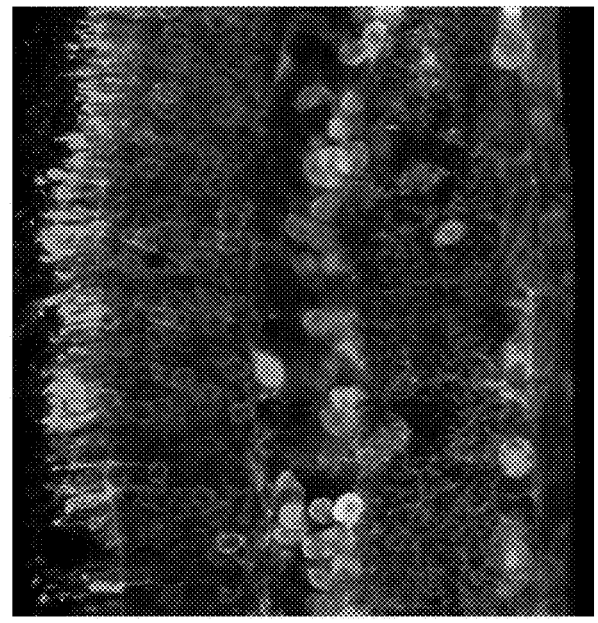
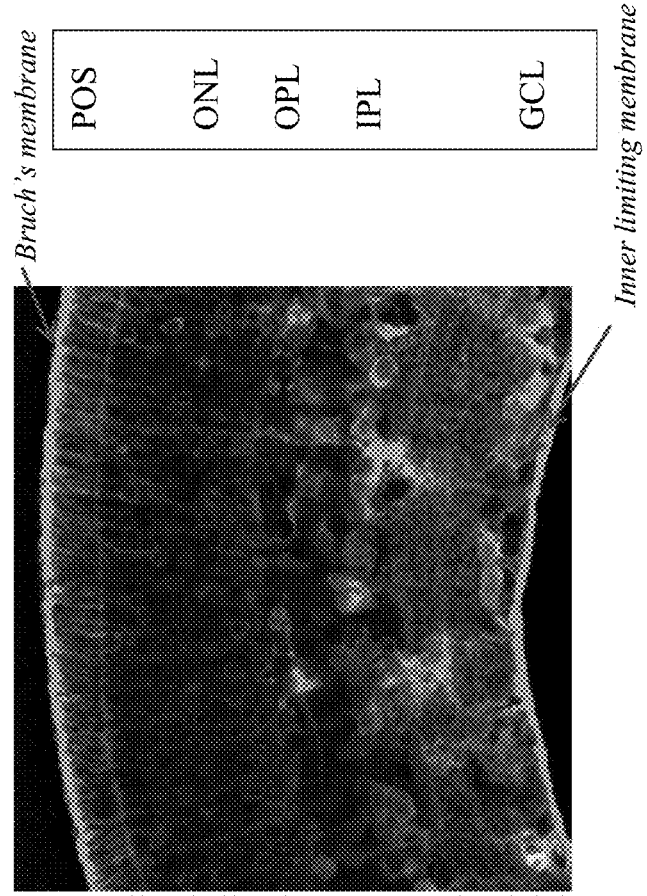

POS

ONL

OPL
*ON-bipolar cell bodies*

IPL
*ON-bipolar cell axons*

*ON-bipolar cell terminals (sublamina 1+2)*
GCL

SEQUENCE LISTING

```
<160> NUMBER OF SEQ ID NOS: 27

<210> SEQ ID NO 1
<211> LENGTH: 9
<212> TYPE: PRT
<213> ORGANISM: Artificial Sequence
<220> FEATURE:
<223> OTHER INFORMATION: AAV-b mutation of AAV aa 587-595

<400> SEQUENCE: 1

Pro Glu Arg Thr Ala Met Ser Leu Pro
1               5

<210> SEQ ID NO 2
<211> LENGTH: 9
<212> TYPE: PRT
<213> ORGANISM: Artificial Sequence
<220> FEATURE:
<223> OTHER INFORMATION: AAV-h mutation at AAV aa 587-595

<400> SEQUENCE: 2

Ser Phe Ser Arg Ala Val Leu Cys Asp
1               5

<210> SEQ ID NO 3
<211> LENGTH: 738
<212> TYPE: PRT
<213> ORGANISM: Artificial Sequence
<220> FEATURE:
<223> OTHER INFORMATION: full length AAV-8b capsid

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60
```

```
Val Asn Ala Ala Asp Ala Ala Leu Glu His Asp Lys Ala Tyr Asp
 65                  70                  75                  80

Gln Gln Leu Gln Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
            450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
```

```
                                485                 490                 495
Gln Asn Asn Asn Ser Asn Phe Ala Trp Thr Ala Gly Thr Lys Tyr His
                500                 505                 510
Leu Asn Gly Arg Asn Ser Leu Ala Asn Pro Gly Ile Ala Met Ala Thr
                515                 520                 525
His Lys Asp Asp Glu Glu Arg Phe Phe Pro Ser Asn Gly Ile Leu Ile
            530                 535                 540
Phe Gly Lys Gln Asn Ala Ala Arg Asp Asn Ala Asp Tyr Ser Asp Val
545                 550                 555                 560
Met Leu Thr Ser Glu Glu Glu Ile Lys Thr Thr Asn Pro Val Ala Thr
                565                 570                 575
Glu Glu Tyr Gly Ile Val Ala Asp Asn Leu Pro Glu Arg Thr Ala Met
                580                 585                 590
Ser Leu Pro Gly Thr Val Asn Ser Gln Gly Ala Leu Pro Gly Met Val
                595                 600                 605
Trp Gln Asn Arg Asp Val Tyr Leu Gln Gly Pro Ile Trp Ala Lys Ile
            610                 615                 620
Pro His Thr Asp Gly Asn Phe His Pro Ser Pro Leu Met Gly Gly Phe
625                 630                 635                 640
Gly Leu Lys His Pro Pro Pro Gln Ile Leu Ile Lys Asn Thr Pro Val
                645                 650                 655
Pro Ala Asp Pro Pro Thr Thr Phe Asn Gln Ser Lys Leu Asn Ser Phe
                660                 665                 670
Ile Thr Gln Tyr Ser Thr Gly Gln Val Ser Val Glu Ile Glu Trp Glu
            675                 680                 685
Leu Gln Lys Glu Asn Ser Lys Arg Trp Asn Pro Glu Ile Gln Tyr Thr
            690                 695                 700
Ser Asn Tyr Tyr Lys Ser Thr Ser Val Asp Phe Ala Val Asn Thr Glu
705                 710                 715                 720
Gly Val Tyr Ser Glu Pro Arg Pro Ile Gly Thr Arg Tyr Leu Thr Arg
                725                 730                 735
Asn Leu

<210> SEQ ID NO 4
<211> LENGTH: 738
<212> TYPE: PRT
<213> ORGANISM: Artificial Sequence
<220> FEATURE:
<223> OTHER INFORMATION: full length AAV-8h capsid

<400> SEQUENCE: 4

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Lys Pro
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Gln Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
```

```
Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
                180                 185                 190

Pro Ala Ala Pro Ser Gly Val Gly Pro Asn Thr Met Ala Ala Gly Gly
                195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
        260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
        340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
        515                 520                 525
```

His Lys Asp Asp Glu Glu Arg Phe Phe Pro Ser Asn Gly Ile Leu Ile
            530                 535                 540
Phe Gly Lys Gln Asn Ala Ala Arg Asp Asn Ala Asp Tyr Ser Asp Val
545                 550                 555                 560
Met Leu Thr Ser Glu Glu Glu Ile Lys Thr Thr Asn Pro Val Ala Thr
                565                 570                 575
Glu Glu Tyr Gly Ile Val Ala Asp Asn Leu Ser Phe Ser Arg Ala Val
            580                 585                 590
Leu Cys Asp Gly Thr Val Asn Ser Gln Gly Ala Leu Pro Gly Met Val
        595                 600                 605
Trp Gln Asn Arg Asp Val Tyr Leu Gln Gly Pro Ile Trp Ala Lys Ile
    610                 615                 620
Pro His Thr Asp Gly Asn Phe His Pro Ser Pro Leu Met Gly Gly Phe
625                 630                 635                 640
Gly Leu Lys His Pro Pro Pro Gln Ile Leu Ile Lys Asn Thr Pro Val
                645                 650                 655
Pro Ala Asp Pro Pro Thr Thr Phe Asn Gln Ser Lys Leu Asn Ser Phe
            660                 665                 670
Ile Thr Gln Tyr Ser Thr Gly Gln Val Ser Val Glu Ile Glu Trp Glu
        675                 680                 685
Leu Gln Lys Glu Asn Ser Lys Arg Trp Asn Pro Glu Ile Gln Tyr Thr
    690                 695                 700
Ser Asn Tyr Tyr Lys Ser Thr Ser Val Asp Phe Ala Val Asn Thr Glu
705                 710                 715                 720
Gly Val Tyr Ser Glu Pro Arg Pro Ile Gly Thr Arg Tyr Leu Thr Arg
                725                 730                 735
Asn Leu

<210> SEQ ID NO 5
<211> LENGTH: 2214
<212> TYPE: DNA
<213> ORGANISM: Artificial Sequence
<220> FEATURE:
<223> OTHER INFORMATION: full length AAV-8b capsid coding sequence

<400> SEQUENCE: 5

```
atggctgccg atggttatct tccagattgg ctcgaggaca acctctctga gggcattcgc    60
gagtggtggg cgctgaaacc tggagccccg aagcccaaag ccaaccagca aaagcaggac   120
gacggccggg gtctggtgct tcctggctac aagtacctcg acccttcaa cggactcgac    180
aagggggagc ccgtcaacgc ggcggacgca gcggccctcg agcacgacaa ggcctacgac   240
cagcagctgc aggcgggtga caatccgtac ctgcggtata ccacgccga cgccgagttt   300
caggagcgtc tgcaagaaga tacgtctttt gggggcaacc tcgggcgagc agtcttccag   360
gccaagaagc gggttctcga acctctcggt ctggttgagg aaggcgctaa gacggctcct   420
ggaaagaaga ccgggtagag ccatcaccc cagcgttctc cagactcctc tacgggcatc   480
ggcaagaaag ccaacagcc gccagaaaaa agactcaatt ttggtcagac tggcgactca   540
gagtcagttc agacccctca acctctcgga gaacctccag cagcgccctc tggtgtggga   600
cctaatacaa tggctgcagg cggtggcgca ccaatggcag acaataacga aggcgccgac   660
ggagtgggta gttcctcggg aaattggcat gcgattcca catggctggg cgacagagtc   720
atcaccacca gcacccgaac ctgggccctg cccacctaca caaccaccct ctacaagcaa   780
atctccaacg ggacatcggg aggagccacc aacgacaaca cctacttcgg ctacagcacc   840
```

```
ccctgggggt attttgactt taacagattc cactgccact tttcaccacg tgactggcag     900
cgactcatca acaacaactg gggattccgg cccaagagac tcagcttcaa gctcttcaac     960
atccaggtca aggaggtcac gcagaatgaa ggcaccaaga ccatcgccaa taacctcacc   1020
agcaccatcc aggtgtttac ggactcggag taccagctgc cgtacgttct cggctctgcc   1080
caccagggct gcctgcctcc gttcccggcg gacgtgttca tgattcccca gtacggctac   1140
ctaacactca caacggtag tcaggccgtg ggacgctcct ccttctactg cctggaatac   1200
tttccttcgc agatgctgag aaccggcaac aacttccagt ttacttacac cttcgaggac   1260
gtgcctttcc acagcagcta cgcccacagc cagagcttgg accggctgat gaatcctctg   1320
attgaccagt acctgtacta cttgtctcgg actcaaacaa caggaggcac ggcaaatacg   1380
cagactctgg gcttcagcca aggtgggcct aatacaatgg ccaatcaggc aaagaactgg   1440
ctgccaggac cctgttaccg ccaacaacgc gtctcaacga caaccgggca aaacaacaat   1500
agcaactttg cctggactgc tgggaccaaa taccatctga atggaagaaa ttcattggct   1560
aatcctggca tcgctatggc aacacacaaa gacgacgagg agcgtttttt tcccagtaac   1620
gggatcctga ttttttggcaa acaaaatgct gccagagaca atgcggatta cagcgatgtc   1680
atgctcacca gcgaggaaga aatcaaaacc actaaccctg tggctacaga ggaatacggt   1740
atcgtggcag ataacttgcc tgagcggacg gcgatgagtc ttccgggaac tgtcaacagc   1800 caggggggcct acccggtat ggtctggcag aaccgggacg tgtacctgca gggtcccatc   1860
tgggccaaga ttcctcacac ggacggcaac ttccacccgt ctccgctgat gggcggcttt   1920
ggcctgaaac atcctccgcc tcagatcctg atcaagaaca cgcctgtacc tgcggatcct   1980
ccgaccacct tcaaccagtc aaagctgaac tctttcatca cgcaatacag caccggacag   2040
gtcagcgtgg aaattgaatg ggagctgcag aaggaaaaca gcaagcgctg gaaccccgag   2100
atccagtaca cctccaacta ctacaaatct acaagtgtgg actttgctgt taatacagaa   2160
ggcgtgtact ctgaaccccg ccccattggc acccgttacc tcacccgtaa tctg         2214

<210> SEQ ID NO 6
<211> LENGTH: 2214
<212> TYPE: DNA
<213> ORGANISM: Artificial Sequence
<220> FEATURE:
<223> OTHER INFORMATION: full length AAV-8h capsid coding sequence

<400> SEQUENCE: 6
atggctgccg atggttatct tccagattgg ctcgaggaca acctctctga gggcattcgc     60
gagtggtggg cgctgaaacc tggagccccg aagcccaaag ccaaccagca aaagcaggac    120
gacggccggg gtctggtgct tcctggctac aagtacctcg acccttcaa cggactcgac    180 aagggggagc ccgtcaacgc ggcggacgca gcggccctcg agcacgacaa ggcctacgac    240
cagcagctgc aggcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tacgggcatc    480
ggcaagaaag gccaacagcc cgccagaaaa agactcaatt ttggtcagac tggcgactca    540
gagtcagttc cagaccctca acctctcgga gaacctccag cagcgccctc tggtgtggga    600
cctaatacaa tggctgcagg cggtggcgca ccaatggcag acaataacga aggcgccgac    660
ggagtgggta gttcctcggg aaattggcat tgcgattcca tggctgggcg acagagtc      720
```

-continued

```
atcaccacca gcacccgaac ctgggccctg cccacctaca acaaccacct ctacaagcaa     780
atctccaacg ggacatcggg aggagccacc aacgacaaca cctacttcgg ctacagcacc     840
ccctgggggt attttgactt taacagattc cactgccact tttcaccacg tgactggcag     900
cgactcatca acaacaactg gggattccgg cccaagagac tcagcttcaa gctcttcaac     960
atccaggtca aggaggtcac gcagaatgaa ggcaccaaga ccatcgccaa taacctcacc    1020
agcaccatcc aggtgtttac ggactcggag taccagctgc cgtacgttct cggctctgcc    1080
caccagggct gcctgcctcc gttcccggcg gacgtgttca tgattcccca gtacggctac    1140
ctaacactca caacggtag tcaggccgtg ggacgctcct ccttctactg cctggaatac    1200
tttccttcgc agatgctgag aaccggcaac aacttccagt ttacttacac cttcgaggac    1260 gtgccttttcc acagcagcta cgcccacagc cagagcttgg accggctgat gaatcctctg    1320
attgaccagt acctgtacta cttgtctcgg actcaaacaa caggaggcac ggcaaatacg    1380
cagactctgg gcttcagcca aggtgggcct aatacaatgg ccaatcaggc aaagaactgg    1440
ctgccaggac cctgttaccg ccaacaacgc gtctcaacga caaccgggca aaacaacaat    1500
agcaactttg cctggactgc tgggaccaaa taccatctga atggaagaaa ttcattggct    1560
aatcctggca tcgctatggc aacacacaaa gacgacgagg agcgtttttt tcccagtaac    1620
gggatcctga tttttggcaa acaaaatgct gccagagaca atgcggatta cagcgatgtc    1680
atgctcacca gcgaggaaga aatcaaaacc actaaccctg tggctacaga ggaatacggt    1740
atcgtggcag ataacttgag ttttagtcgt gcggttcttt gtgatggaac tgtcaacagc    1800 caggggcct acccggtat ggtctggcag aaccgggacg tgtacctgca gggtcccatc    1860
tgggccaaga ttcctcacac ggacggcaac ttccacccgt ctccgctgat gggcggcttt    1920
ggcctgaaac atcctccgcc tcagatcctg atcaagaaca cgcctgtacc tgcggatcct    1980
ccgaccacct tcaaccagtc aaagctgaac tctttcatca cgcaatacag caccggacag    2040
gtcagcgtgg aaattgaatg ggagctgcag aaggaaaaca gcaagcgctg gaaccccgag    2100
atccagtaca cctccaacta ctacaaatct acaagtgtgg actttgctgt taatacagaa    2160
ggcgtgtact ctgaaccccg ccccattggc acccgttacc tcacccgtaa tctg          2214
```

<210> SEQ ID NO 7
<211> LENGTH: 2213
<212> TYPE: DNA
<213> ORGANISM: adeno-associated virus 8

<400> SEQUENCE: 7

```
atggctgccg atggttatct tccagattgg ctcgaggaca acctctctga gggcattcgc     60
gagtggtggg cgctgaaacc tggagccccg aagcccaaag ccaaccagca aaagcaggac    120
gacggccggg gtctggtgct tcctggctac aagtacctcg accccttcaa cggactcgac    180 aaggggagc ccgtcaacgc ggcggacgca gcggccctcg agcacgacaa ggcctacgac    240
cagcagctgc aggcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tacgggcatc    480
ggcaagaaag gccaacagcc cgccagaaaa agactcaatt ttggtcagac tggcgactca    540
gagtcagttc cagaccctca acctctcgga gaacctccag cagcgccctc tggtgtggga    600
```

-continued

```
cctaatacaa tggctgcagg cggtggcgca ccaatggcag acaataacga aggcgccgac    660
ggagtgggta gttcctcggg aaattggcat tgcgattcca catggctggg cgacagagtc    720
atcaccacca gcacccgaac ctgggccctg cccacctaca caaccacct ctacaagcaa     780
atctccaacg ggacatcggg aggagccacc aacgacaaca cctacttcgg ctacagcacc    840
ccctgggggt attttgactt taacagattc cactgccact tttcaccacg tgactggcag    900
cgactcatca caacaactg gggattccgg cccaagagac tcagcttcaa gctcttcaac     960
atccaggtca aggaggtcac gcagaatgaa ggcaccaaga ccatcgccaa taacctcacc    1020
agcaccatcc aggtgtttac ggactcgag taccagctgc cgtacgttct cggctctgcc     1080
caccagggct gcctgcctcc gttcccggcg gacgtgttca tgattcccca gtacggctac    1140
ctaacactca caacggtag tcaggccgtg ggacgctcct ccttctactg cctggaatac     1200
tttccttcgc agatgctgag aaccggcaac aacttccagt ttacttacac cttcgaggac    1260
gtgcctttcc acagcagcta cgcccacagc cagagcttgg accggctgat gaatcctctg    1320
attgaccagt acctgtacta cttgtctcgg actcaaacaa caggaggcac ggcaaatacg    1380
cagactctgg gcttcagcca aggtgggcct aatacaatgg ccaatcaggc aaagaactgg    1440
ctgccaggac cctgttaccg ccaacaacgc gtctcaacga caaccgggca aaacaacaat    1500
agcaactttg cctggactgc tgggaccaaa taccatctga atggaagaaa ttcattggct    1560
aatcctggca tcgctatggc aacacacaaa gacgacgagg agcgtttttt tcccagtaac    1620
gggatcctga tttttggcaa acaaaatgct gccagagaca atgcggatta cagcgatgtc    1680
atgctcacca gcgaggaaga aatcaaaacc actaaccctg tggctacaga ggaatacggt    1740
atcgtggcag ataacttgca gcagcaaaac acggctcctc aaattggaac tgtcaacagc    1800
caggggcct acccggtat ggtctggcag aaccggacg tgtacctgca gggtcccatc       1860
tgggccaaga ttcctcacac ggacggcaac ttccaccgt ctccgctgat gggcggcttt    1920
ggcctgaaac atcctccgcc tcagatcctg atcaagaaca cgcctgtacc tgcggatcct    1980
ccgaccacct tcaaccagtc aaagctgaac tctttcatca cgcaatacag caccggacag    2040
gtcagcgtgg aaattgaatg ggagctgcag aaggaaaaca gcaagcgctg gaaccccgag    2100
atccagtaca cctccaacta ctacaaatct acaagtgtgg actttgctgt aatacagaag    2160
gcgtgtactc tgaaccccgc cccattggca cccgttacct cacccgtaat ctg           2213
```

<210> SEQ ID NO 8
<211> LENGTH: 737
<212> TYPE: PRT
<213> ORGANISM: adeno-associated virus 8

<400> SEQUENCE: 8

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95
```

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
                195                 200                 205

Gly Ala Pro Met Ala Asp Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510
```

```
Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
            565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                    645                 650                 655

Pro Ala Asp Pro Pro Thr Thr Phe Asn Gln Ser Lys Leu Asn Ser Phe
                    660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Ser Val Asp Phe Ala Val Ile Gln Lys
705                 710                 715                 720

Ala Cys Thr Leu Asn Pro Ala Pro Leu Ala Pro Val Thr Ser Pro Val
                    725                 730                 735

Ile

<210> SEQ ID NO 9
<211> LENGTH: 27
<212> TYPE: DNA
<213> ORGANISM: Artificial Sequence
<220> FEATURE:
<223> OTHER INFORMATION: AAV-b aa 587-595 codiing sequence

<400> SEQUENCE: 9
cctgagcgga cggcgatgag tcttccg                                      27

<210> SEQ ID NO 10
<211> LENGTH: 27
<212> TYPE: DNA
<213> ORGANISM: Artificial Sequence
<220> FEATURE:
<223> OTHER INFORMATION: AAV-h aa 587-595 codiing sequence

<400> SEQUENCE: 10
agttttagtc gtgcggttct ttgtgat                                      27

<210> SEQ ID NO 11
<211> LENGTH: 27
<212> TYPE: DNA
<213> ORGANISM: adeno-associated virus 8

<400> SEQUENCE: 11
cagcagcaaa acacggctcc tcaaatt                                      27
```

```
<210> SEQ ID NO 12
<211> LENGTH: 9
<212> TYPE: PRT
<213> ORGANISM: adeno-associated virus 8

<400> SEQUENCE: 12

Gln Gln Gln Asn Thr Ala Pro Gln Ile
1               5

<210> SEQ ID NO 13
<211> LENGTH: 27
<212> TYPE: DNA
<213> ORGANISM: Artificial Sequence
<220> FEATURE:
<223> OTHER INFORMATION: constructed sequence

<400> SEQUENCE: 13
tatcttatgc gttatattgg tgttttt                                        27

<210> SEQ ID NO 14
<211> LENGTH: 9
<212> TYPE: PRT
<213> ORGANISM: Artificial Sequence
<220> FEATURE:
<223> OTHER INFORMATION: constructed sequence

<400> SEQUENCE: 14

Tyr Leu Met Arg Tyr Ile Gly Gly Phe
1               5

<210> SEQ ID NO 15
<211> LENGTH: 27
<212> TYPE: DNA
<213> ORGANISM: Artificial Sequence
<220> FEATURE:
<223> OTHER INFORMATION: constructed sequence

<400> SEQUENCE: 15
cattgtgtgg attgttgtgc gtcttat                                        27

<210> SEQ ID NO 16
<211> LENGTH: 9
<212> TYPE: PRT
<213> ORGANISM: Artificial Sequence
<220> FEATURE:
<223> OTHER INFORMATION: constructed sequence

<400> SEQUENCE: 16

His Cys Val Asp Cys Cys Ala Ser Tyr
1               5

<210> SEQ ID NO 17
<211> LENGTH: 27
<212> TYPE: DNA
<213> ORGANISM: Artificial Sequence
<220> FEATURE:
<223> OTHER INFORMATION: constructed sequence

<400> SEQUENCE: 17
catactgagt atatgagtga gtagctc                                        27

<210> SEQ ID NO 18
<211> LENGTH: 8
<212> TYPE: PRT
<213> ORGANISM: Artificial Sequence
<220> FEATURE:
<223> OTHER INFORMATION: constructed sequence
```

-continued

<400> SEQUENCE: 18

His Thr Glu Tyr Met Ser Glu Leu
1               5

<210> SEQ ID NO 19
<211> LENGTH: 27
<212> TYPE: DNA
<213> ORGANISM: Artificial Sequence
<220> FEATURE:
<223> OTHER INFORMATION: constructed sequence

<400> SEQUENCE: 19 ccgattttg ttgggtgttc tgtgctt                                           27

<210> SEQ ID NO 20
<211> LENGTH: 9
<212> TYPE: PRT
<213> ORGANISM: Artificial Sequence
<220> FEATURE:
<223> OTHER INFORMATION: constructed sequence

<400> SEQUENCE: 20

Pro Ile Phe Val Gly Cys Ser Val Leu
1               5

<210> SEQ ID NO 21
<211> LENGTH: 736
<212> TYPE: PRT
<213> ORGANISM: adeno-associated virus 1

<400> SEQUENCE: 21

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala

-continued

```
                210                 215                 220
Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
                275                 280                 285

His Cys His Phe Ser Pro Arg Asp Trp Gln Arg Leu Ile Asn Asn Asn
                290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
                370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
                435                 440                 445

Thr Gln Asn Gln Ser Gly Ser Ala Gln Asn Lys Asp Leu Leu Phe Ser
                450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
                515                 520                 525

Asp Asp Glu Asp Lys Phe Phe Pro Met Ser Gly Val Met Ile Phe Gly
                530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
                580                 585                 590

Thr Gly Asp Val His Ala Met Gly Ala Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly His Phe His Pro Ser Pro Leu Met Gly Gly Phe Gly Leu
625                 630                 635                 640
```

```
Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 22
<211> LENGTH: 735
<212> TYPE: PRT
<213> ORGANISM: adeno-associated virus 2

<400> SEQUENCE: 22

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
```

```
                  275                 280                 285
        Cys His Phe Ser Pro Arg Asp Trp Gln Arg Leu Ile Asn Asn Asn Trp
        290                 295                 300
        Gly Phe Arg Pro Lys Arg Leu Asn Phe Lys Leu Phe Asn Ile Gln Val
        305                 310                 315                 320
        Lys Glu Val Thr Gln Asn Asp Gly Thr Thr Thr Ile Ala Asn Asn Leu
                        325                 330                 335
        Thr Ser Thr Val Gln Val Phe Thr Asp Ser Glu Tyr Gln Leu Pro Tyr
                    340                 345                 350
        Val Leu Gly Ser Ala His Gln Gly Cys Leu Pro Pro Phe Pro Ala Asp
                355                 360                 365
        Val Phe Met Val Pro Gln Tyr Gly Tyr Leu Thr Leu Asn Asn Gly Ser
            370                 375                 380
        Gln Ala Val Gly Arg Ser Ser Phe Tyr Cys Leu Glu Tyr Phe Pro Ser
        385                 390                 395                 400
        Gln Met Leu Arg Thr Gly Asn Asn Phe Thr Phe Ser Tyr Thr Phe Glu
                        405                 410                 415
        Asp Val Pro Phe His Ser Ser Tyr Ala His Ser Gln Ser Leu Asp Arg
                    420                 425                 430
        Leu Met Asn Pro Leu Ile Asp Gln Tyr Leu Tyr Tyr Leu Ser Arg Thr
                435                 440                 445
        Asn Thr Pro Ser Gly Thr Thr Thr Gln Ser Arg Leu Gln Phe Ser Gln
            450                 455                 460
        Ala Gly Ala Ser Asp Ile Arg Asp Gln Ser Arg Asn Trp Leu Pro Gly
        465                 470                 475                 480
        Pro Cys Tyr Arg Gln Gln Arg Val Ser Lys Thr Ser Ala Asp Asn Asn
                        485                 490                 495
        Asn Ser Glu Tyr Ser Trp Thr Gly Ala Thr Lys Tyr His Leu Asn Gly
                    500                 505                 510
        Arg Asp Ser Leu Val Asn Pro Gly Pro Ala Met Ala Ser His Lys Asp
                515                 520                 525
        Asp Glu Glu Lys Phe Phe Pro Gln Ser Gly Val Leu Ile Phe Gly Lys
            530                 535                 540
        Gln Gly Ser Glu Lys Thr Asn Val Asp Ile Glu Lys Val Met Ile Thr
        545                 550                 555                 560
        Asp Glu Glu Glu Ile Arg Thr Thr Asn Pro Val Ala Thr Glu Gln Tyr
                        565                 570                 575
        Gly Ser Val Ser Thr Asn Leu Gln Arg Gly Asn Arg Gln Ala Ala Thr
                    580                 585                 590
        Ala Asp Val Asn Thr Gln Gly Val Leu Pro Gly Met Val Trp Gln Asp
                595                 600                 605
        Arg Asp Val Tyr Leu Gln Gly Pro Ile Trp Ala Lys Ile Pro His Thr
            610                 615                 620
        Asp Gly His Phe His Pro Ser Pro Leu Met Gly Gly Phe Gly Leu Lys
        625                 630                 635                 640
        His Pro Pro Pro Gln Ile Leu Ile Lys Asn Thr Pro Val Pro Ala Asn
                        645                 650                 655
        Pro Ser Thr Thr Phe Ser Ala Ala Lys Phe Ala Ser Phe Ile Thr Gln
                    660                 665                 670
        Tyr Ser Thr Gly Gln Val Ser Val Glu Ile Glu Trp Glu Leu Gln Lys
                675                 680                 685
        Glu Asn Ser Lys Arg Trp Asn Pro Glu Ile Gln Tyr Thr Ser Asn Tyr
            690                 695                 700
```

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 23
<211> LENGTH: 736
<212> TYPE: PRT
<213> ORGANISM: adeno-associated virus 3

<400> SEQUENCE: 23

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
                20                  25                  30

Lys Ala Asn Gln Gln His Gln Asp Asn Arg Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr

```
                        340                 345                 350
    Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
    385                 390                 395                 400

Gln Met Leu Arg Thr Gly Asn Asn Phe Gln Phe Ser Tyr Thr Phe Glu
                    405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
    465                 470                 475                 480

Gly Pro Cys Tyr Arg Gln Gln Arg Leu Ser Lys Thr Ala Asn Asp Asn
                    485                 490                 495

Asn Asn Ser Asn Phe Pro Trp Thr Ala Ala Ser Lys Tyr His Leu Asn
                500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
    545                 550                 555                 560

Thr Asp Glu Glu Glu Ile Arg Thr Thr Asn Pro Val Ala Thr Glu Gln
                    565                 570                 575

Tyr Gly Thr Val Ala Asn Asn Leu Gln Ser Ser Asn Thr Ala Pro Thr
                580                 585                 590

Thr Gly Thr Val Asn His Gln Gly Ala Leu Pro Gly Met Val Trp Gln
            595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
    625                 630                 635                 640

Lys His Pro Pro Pro Gln Ile Met Ile Lys Asn Thr Pro Val Pro Ala
                    645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
    705                 710                 715                 720

Tyr Ser Glu Pro Arg Pro Ile Gly Thr Arg Tyr Leu Thr Arg Asn Leu
                    725                 730                 735

<210> SEQ ID NO 24
<211> LENGTH: 736
<212> TYPE: PRT
<213> ORGANISM: adeno-associated virus 3B
```

<400> SEQUENCE: 24

| | | | | | | | | | | | | | |
|---|---|---|---|---|---|---|---|---|---|---|---|---|---|
|Met|Ala|Ala|Asp|Gly|Tyr|Leu|Pro|Asp|Trp|Leu|Glu|Asp|Asn|Leu|Ser|
|1| | | |5| | | | |10| | | | |15| |

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Ile Leu Glu Pro
    115                 120                 125

Leu Gly Leu Val Glu Glu Ala Ala Lys Thr Ala Pro Gly Lys Lys Arg
130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
            165                 170                 175

Gly Asp Ser Glu Ser Val Pro Asp Pro Gln Pro Leu Gly Glu Pro Pro
        180                 185                 190

Ala Ala Pro Thr Ser Leu Gly Ser Asn Thr Met Ala Ser Gly Gly Gly
    195                 200                 205

Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
        260                 265                 270

Phe Gly Tyr Ser Thr Pro Trp Gly Tyr Phe Asp Phe Asn Arg Phe His
    275                 280                 285

Cys His Phe Ser Pro Arg Asp Trp Gln Arg Leu Ile Asn Asn Asn Trp
290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
        340                 345                 350

Val Leu Gly Ser Ala His Gln Gly Cys Leu Pro Pro Phe Pro Ala Asp
    355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu 405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 25
<211> LENGTH: 734
<212> TYPE: PRT
<213> ORGANISM: adeno-associated virus 4

<400> SEQUENCE: 25

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

```
Tyr Lys Tyr Leu Gly Pro Gly Asn Gly Leu Asp Lys Gly Glu Pro Val
    50                  55                  60

Asn Ala Asp Ala Ala Ala Leu Glu His Asp Lys Ala Tyr Asp Gln
65              70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
            115                 120                 125

Gly Leu Val Glu Gln Ala Gly Glu Thr Ala Pro Gly Lys Lys Arg Pro
130                 135                 140

Leu Ile Glu Ser Pro Gln Pro Asp Ser Ser Thr Gly Ile Gly Lys
145                 150                 155                 160

Lys Gly Lys Gln Pro Ala Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Gly Gly Ala Ala Val Glu Gly
            195                 200                 205

Gly Gln Gly Ala Asp Gly Val Gly Asn Ala Ser Gly Asp Trp His Cys
            210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
            275                 280                 285

Arg Leu Ile Asn Asn Asn Trp Gly Met Arg Pro Lys Ala Met Arg Val
            290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
            355                 360                 365

Cys Gly Leu Val Thr Gly Asn Thr Ser Gln Gln Gln Thr Asp Arg Asn
370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
            435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
```

```
                465                 470                 475                 480
Gln Gly Phe Ser Lys Thr Ala Asn Gln Asn Tyr Lys Ile Pro Ala Thr
                    485                 490                 495
Gly Ser Asp Ser Leu Ile Lys Tyr Glu Thr His Ser Thr Leu Asp Gly
                500                 505                 510
Arg Trp Ser Ala Leu Thr Pro Gly Pro Pro Met Ala Thr Ala Gly Pro
            515                 520                 525
Ala Asp Ser Lys Phe Ser Asn Ser Gln Leu Ile Phe Ala Gly Pro Lys
        530                 535                 540
Gln Asn Gly Asn Thr Ala Thr Val Pro Gly Thr Leu Ile Phe Thr Ser
545                 550                 555                 560
Glu Glu Glu Leu Ala Ala Thr Asn Ala Thr Asp Thr Asp Met Trp Gly
                565                 570                 575
Asn Leu Pro Gly Gly Asp Gln Ser Asn Ser Asn Leu Pro Thr Val Asp
                580                 585                 590
Arg Leu Thr Ala Leu Gly Ala Val Pro Gly Met Val Trp Gln Asn Arg
            595                 600                 605
Asp Ile Tyr Tyr Gln Gly Pro Ile Trp Ala Lys Ile Pro His Thr Asp
        610                 615                 620
Gly His Phe His Pro Ser Pro Leu Ile Gly Gly Phe Gly Leu Lys His
625                 630                 635                 640
Pro Pro Pro Gln Ile Phe Ile Lys Asn Thr Pro Val Pro Ala Asn Pro
                645                 650                 655
Ala Thr Thr Phe Ser Ser Thr Pro Val Asn Ser Phe Ile Thr Gln Tyr
                660                 665                 670
Ser Thr Gly Gln Val Ser Val Gln Ile Asp Trp Glu Ile Gln Lys Glu
            675                 680                 685
Arg Ser Lys Arg Trp Asn Pro Glu Val Gln Phe Thr Ser Asn Tyr Gly
        690                 695                 700
Gln Gln Asn Ser Leu Leu Trp Ala Pro Asp Ala Ala Gly Lys Tyr Thr
705                 710                 715                 720
Glu Pro Arg Ala Ile Gly Thr Arg Tyr Leu Thr His His Leu
                725                 730

<210> SEQ ID NO 26
<211> LENGTH: 736
<212> TYPE: PRT
<213> ORGANISM: adeno-associated virus 6

<400> SEQUENCE: 26

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
```

```
Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
```

```
                530             535             540
Lys Glu Ser Ala Gly Ala Ser Asn Thr Ala Leu Asp Asn Val Met Ile
545                 550                 555                 560

Thr Asp Glu Glu Ile Lys Ala Thr Asn Pro Val Ala Thr Glu Arg
                565                 570                 575

Phe Gly Thr Val Ala Val Asn Leu Gln Ser Ser Thr Asp Pro Ala
                580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
                610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                    645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Val Gln Tyr Thr Ser Asn
                690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                    725                 730                 735

<210> SEQ ID NO 27
<211> LENGTH: 737
<212> TYPE: PRT
<213> ORGANISM: adeno-associated virus 7

<400> SEQUENCE: 27

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175
```

```
Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
            195                 200                 205

Gly Ala Pro Met Ala Asp Asn Asn Glu Gly Ala Asp Gly Val Gly Asn
            210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
            370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
            450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
            530                 535                 540

Phe Gly Lys Thr Gly Ala Thr Asn Lys Thr Thr Leu Glu Asn Val Leu
545                 550                 555                 560

Met Thr Asn Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
```

```
              595                 600                 605
Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu
```

ENHANCED AAV-MEDIATED GENE TRANSFER FOR RETINAL THERAPIES

CROSS-REFERENCE TO RELATED APPLICATIONS

This application is a divisional of U.S. patent application Ser. No. 14/766,172, filed Aug. 6, 2015, which is a US national phase of International Patent Application No. PCT/US2014/15340, filed Feb. 7, 2014, which claims the benefit of the priority of U.S. Provisional Patent Application No. 61/762,775, filed Feb. 8, 2013. These priority applications are incorporated by reference herein.

BACKGROUND OF THE INVENTION

Recombinant Adeno-Associated Virus (rAAV) vectors have been instrumental in achieving restoration of vision in humans with Leber's congenital amaurosis due to RPE65 mutations and in a number of animal models (reviewed by Stieger, K. et al, Adeno-associated virus mediated gene therapy for retinal degenerative diseases. Methods Mol Biol 807, 179-218 (2011) which is incorporated by reference herein). The first retinal gene therapy clinical trials for retinal degenerative disease were initiated in humans in 2007 using AAV2 to deliver test the safety of therapeutic gene expression in children and adults with an early form of blindness called Leber's Congenital Amaurosis. Now, five years later, there are 7 Phase I/II gene therapy trials in progress involving inherited blindness. The first Phase III clinical trial initiated enrollment in the fourth quarter of 2012 (http://clinicaltrials.gov) and the results to date have been excellent. More than 125 individuals have already participated in retinal gene AAV-mediated gene therapy clinical trials and the safety records in these studies have been excellent.

Given the excellent safety and efficacy data relating to AAV-mediated retinal gene therapy and given the large number of inherited and acquired diseases that lead to blindness, there are many additional targets and strategies that are under consideration for application to the retina. One challenge, however, is to identify vectors which can efficiently and stably transduce a large variety of retinal cell types. Many of the rAAVs that have been characterized to date target retinal pigment epithelium (RPE) cells efficiently, and several of them target rod photoreceptors efficiently. One (AAV2) targets ganglion cells, a few target Muller cells (AAV2, AAV5, AAV8), and another (AAV9) targets cone photoreceptors. However, few AAVs have been found that target a majority of ocular cells with high efficiency.

In a normal eye, photoreceptors form the outermost layer of the retina. They convert light into electrical signals, which are sent to neurons in the retina's middle layer known as bipolar cells. Bipolar cells send visual information to the inner layer, made up of ganglion cells, which then connect to the brain via the optic nerve. In optogenetic therapy, artificial photoreceptors are constructed by gene delivery of light-activated channels or pumps to surviving cell types in the remaining retinal circuit. Because the bipolar cells are involved in processing visual signals, they have become the focus of attention from those interested in optogenetic therapies for the retina. However, so far, no recombinant virus has been identified which transduces bipolar cells of the retina.

Horizontal cells present an interesting target. Although, to date, no horizontal cell-specific genes are known that contribute to retinal disease, 40 genes are still unidentified from the 232 loci that are currently linked to retinal disease, and disease genes may yet be discovered in horizontal cells (https://sph.uth.edu/retnet/sum-dis.htm). Further, horizontal cells adjust photoreceptor output through feedback signals and are crucial to vision perception. More information is needed about horizontal cells to fully understand visual perception. Thus, the ability to express desired transgenes in these, and other ocular cell types, is needed.

SUMMARY OF THE INVENTION

In one aspect, a recombinant AAV capsid protein is provided. The AAV capsid protein is characterized by a mutation in aa 587-595 as compared to the wild type AAV8 capsid sequence, or a mutation in the analogous region of another AAV capsid as compared to the corresponding AAV wild type capsid sequence. In one embodiment, the AAV capsid protein is characterized by a mutation in nt 1759-1785 of the sequence coding for the AAV8 capsid protein as compared to the AAV8 wild type sequence, or a mutation in the analogous region of the sequence coding for another AAV capsid as compared to the corresponding AAV wild type capsid sequence. In another embodiment, the recombinant AAV capsid protein is characterized by at least one mutation in the HI loop as compared to the wild type sequence. In another embodiment, the recombinant AAV capsid protein comprises SEQ ID NO: 1 or SEQ ID NO: 2. In another embodiment, the recombinant AAV capsid protein comprises SEQ ID NO: 3 or SEQ ID NO: 4.

In another aspect, nucleic acid sequences are provided encoding any of the recombinant AAV capsid proteins as described herein.

In another aspect, recombinant adeno-associated viruses (AAV) are provided. In one embodiment, the AAV has a recombinant AAV capsid having a mutation in aa 587-595 of the AAV8 capsid protein sequence as compared to the AAV8 wild type capsid sequence or a mutation in a corresponding region of another AAV capsid protein as compared to the corresponding wild type capsid sequence. The AAV further has a minigene having AAV inverted terminal repeats and a heterologous nucleic acid sequence operably linked to regulatory sequences which direct expression of a product encoded by the heterologous nucleic acid sequence in a target cell or tissue. In one embodiment, the AAV has a capsid protein comprising the sequence of SEQ ID NO: 1 or SEQ ID NO: 2. In another embodiment, the AAV has a capsid protein having the sequence of SEQ ID NO: 3 or SEQ ID NO: 4.

In yet another aspect, a method of preventing, arresting progression of, or ameliorating vision loss associated with an ocular disorder in a subject is provided. The method includes administering to the subject an effective concentration of a composition comprising any recombinant adeno-associated virus (AAV) described herein and a pharmaceutically acceptable carrier.

In another aspect, a method of targeting bipolar cells for optogenetic therapy in a subject in need thereof is provided. The method includes administering to the subject an effective concentration of a composition comprising any of the recombinant adeno-associated virus (AAV) described herein and a pharmaceutically acceptable carrier.

In another aspect, a method of targeting one or more type of ocular cells for optogenetic therapy in a subject in need thereof is provided. The method includes administering to the subject an effective concentration of a composition comprising any of the recombinant adeno-associated virus (AAV) described herein and a pharmaceutically acceptable carrier.

In another aspect, a method of targeting one or more type of ocular cells for gene augmentation therapy in a subject in need thereof is provided. The method includes administering to the subject an effective concentration of a composition comprising any of the recombinant adeno-associated virus (AAV) described herein and a pharmaceutically acceptable carrier.

In yet another aspect, a method of targeting one or more type of ocular cells for gene suppression therapy in a subject in need thereof is provided. The method includes administering to the subject an effective concentration of a composition comprising any of the recombinant adeno-associated virus (AAV) described herein and a pharmaceutically acceptable carrier.

In another aspect, a method of targeting one or more type of ocular cells for gene knockdown/augmentation therapy in a subject in need thereof is provided. The method includes administering to the subject an effective concentration of a composition comprising any of the recombinant adeno-associated virus (AAV) described herein and a pharmaceutically acceptable carrier.

In another aspect, a method of targeting one or more type of ocular cells for gene correction therapy in a subject in need thereof is provided. The method includes administering to the subject an effective concentration of a composition comprising any of the recombinant adeno-associated virus (AAV) described herein and a pharmaceutically acceptable carrier.

In yet another aspect, a method of targeting one or more type of ocular cells for neurotropic factor gene therapy in a subject in need thereof is provided. The method includes administering to the subject an effective concentration of a composition comprising any of the recombinant adeno-associated virus (AAV) described herein and a pharmaceutically acceptable carrier.

In another aspect, a method of targeting all ocular cells for optogenetic therapy in a subject in need thereof is provided. The method includes administering to the subject an effective concentration of a composition comprising any of the recombinant adeno-associated virus (AAV) described herein and a pharmaceutically acceptable carrier.

In another aspect, a method of generating a recombinant adeno-associated virus (rAAV) having an AAV capsid is provided. The method includes the steps of culturing a host cell containing: (a) a molecule encoding an AAV capsid protein as described herein; (b) a functional rep gene; (c) a minigene comprising AAV inverted terminal repeats (ITRs) and a heterologous nucleic acid sequence operably linked to regulatory sequences which direct expression of a product encoded by the heterologous nucleic acid sequence in a target cell; and (d) sufficient helper functions to permit packaging of the minigene into the AAV capsid protein.

In another aspect, a host or target cell transfected with an AAV or nucleic acid molecule as described herein is provided.

In another aspect, a composition is provided comprising an AAV as described herein and a physiologically compatible carrier.

In another aspect, a method of delivering a transgene to a cell is provided. The method includes the step of contacting the cell with an AAV according as described herein, wherein said AAV comprises the minigene.

In yet another aspect, the use of the AAV or a nucleic acid molecule as described herein is provided for preparing a medicament for delivery of a heterologous nucleic acid molecule encoding the product to a cell.

BRIEF DESCRIPTION OF THE FIGURES

FIG. 1 is an alignment of the variable protein 1 (vp1) capsid protein for AAV1, AAV2, AAV3, AAV3B, AAV4, AAV6, AAV7 and AAV8 taken from Gao G et al. PNAS, September 2002; 99:11854-11859. The region of mutation (aa 587-595 of AAV8 wt sequence) is boxed.

FIG. 5 shows the sequences of aa 587-595 of the 5 "double positive" variants sequenced as discussed in Example 2. The wild type sequence of AAV8 was replaced with each variant sequence. The top line of each sequence shows the DNA coding sequence, the middle row shows the corresponding amino acid and the bottom row provides information regarding the characteristics of the amino acid. P=Polar, N=Non-polar, A=acidic, B=basic, *=very hydrophobic, and ^=hydrophilic. Variant 5 encodes a premature stop codon and was used as a negative control. Variant 6 failed to produce high titer AAV, and no additional testing was done on this mutant.

FIG. 7 are two photographs of 20× images from mouse retinal sections 3 weeks after subretinal injection with either AAV8 wt-EF1α.EGFP (left) or AAV8-b-EF1α.EGFP (right). The various retinal sections are labeled. Abbreviations the same as in FIG. 6. Fluorescence staining shows a strong transduction of the Bruch's membrane and the inner limiting membrane of mouse retina by AAV8 wt-EF1α.EGFP. These membranes are not fluorescent in retinas transduced with AAV8b-EF1α.EGFP. This may account for the greater diffusion of the AAV8b virus through the retina with stronger fluorescence in the region between the inner and outer plexiform layers for AAV8b compared to AAV8 wt. Note that these retinas were also labeled for acetyl choline transferase to identify the region between the inner and outer plexiform layers.

FIG. 9A shows strongly GFP-positive cone photoreceptors, inner retinal cells, and ganglion cells. Additional positive inner nuclear and ganglion cells are appreciated that have less intense GFP expression. The ONL is the same thickness as that in the untreated retina, demonstrating that there are no retinal degenerative changes. There are few if any GFP-positive RPE cells. RPE, retinal pigment epithelium; ONL, outer nuclear layer; INL, inner nuclear layer; GCL, ganglion cell layer.

DETAILED DESCRIPTION OF THE INVENTION

Figure 2:
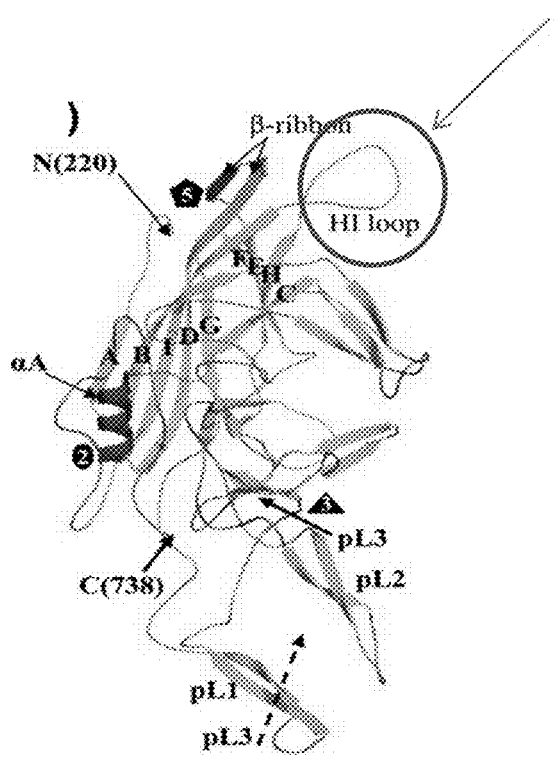
FIG. 2 shows the protein structure of the AAV8 capsid protein taken from Nam, H. J. et al (2007) J. Virol. 81: 12260-12271. The HI (or, alternatively GH) loop, which is the subject of mutation in this invention, is circled.

The present invention relates to various compositions and treatment methods utilizing the same comprising an effective concentration of a recombinant adeno-associated virus (rAAV) characterized by a mutation in aa 587-595 of the capsid protein sequence as compared to the wild type AAV8 capsid sequence, or a mutation in the analogous region of another AAV capsid as compared to the corresponding AAV wild type capsid sequence. The methods are directed to use of the AAV to treat ocular disorders and associated conditions related thereto.

Unless defined otherwise, technical and scientific terms used herein have the same meaning as commonly understood by one of ordinary skill in the art to which this invention belongs and by reference to published texts, which provide one skilled in the art with a general guide to many of the terms used in the present application. The following definitions are provided for clarity only and are not intended to limit the claimed invention. As used herein, the terms "a" or "an", refers to one or more, for example, "an ocular cell" is understood to represent one or more ocular cells. As such, the terms "a" (or "an"), "one or more," and "at least one" are used interchangeably herein. As used herein, the term "about" means a variability of 10% from the reference given, unless otherwise specified. While various embodiments in the specification are presented using "comprising" language, under other circumstances, a related embodiment is also intended to be interpreted and described using "consisting of" or "consisting essentially of" language.

With regard to the following description, it is intended that each of the compositions herein described, is useful, in another embodiment, in the methods of the invention. In addition, it is also intended that each of the compositions herein described as useful in the methods, is, in another embodiment, itself an embodiment of the invention.

As used herein, the term "ocular cells" refers to any cell in, or associated with the function of, the eye. The term may refer to any one or more of photoreceptor cells, including rod, cone and photosensitive ganglion cells, retinal pigment epithelium (RPE) cells, Mueller cells, bipolar cells, horizontal cells, amacrine cells. In one embodiment, the ocular cells are bipolar cells. In another embodiment, the ocular cells are horizontal cells. In another embodiment, the ocular cells are ganglion cells.

As used herein, the term "mammalian subject" or "subject" includes any mammal in need of the methods of treatment described herein or prophylaxis, including particularly humans. Other mammals in need of such treatment or prophylaxis include dogs, cats, or other domesticated animals, horses, livestock, laboratory animals, including non-human primates, etc. The subject may be male or female.

In one embodiment, the subject has, or is at risk of developing an ocular disorder. The term "ocular disorder" includes, without limitation, retinitis pigmentosa, rod-cone dystrophy, Leber's congenital amaurosis, Usher's syndrome, Bardet-Biedl Syndrome, Best disease, retinoschisis, Stargardt disease (autosomal dominant or autosomal recessive), untreated retinal detachment, pattern dystrophy, cone-rod dystrophy, achromatopsia, ocular albinism, enhanced S cone syndrome, diabetic retinopathy, age-related macular degeneration, retinopathy of prematurity, sickle cell retinopathy, Congenital Stationary Night Blindness, glaucoma, or retinal vein occlusion. In another embodiment, the subject has, or is at risk of developing glaucoma, Leber's hereditary optic neuropathy, lysosomal storage disorder, or peroxisomal disorder. In another embodiment, the subject is in need of optogenetic therapy.

As used herein, the term "host cell" may refer to the packaging cell line in which the rAAV is produced from the plasmid. In the alternative, the term "host cell" may refer to the target cell in which expression of the transgene is desired.

In another embodiment, the subject has shown clinical signs of an ocular disorder. Clinical signs of an ocular disorder include, but are not limited to, decreased peripheral vision, decreased central (reading) vision, decreased night vision, loss of color perception, reduction in visual acuity, decreased photoreceptor function, and pigmentary changes. In one embodiment, the subject shows degeneration of the outer nuclear layer (ONL). In another embodiment, the subject has been diagnosed with an ocular disorder. In yet another embodiment, the subject has not yet shown clinical signs of an ocular disorder.

In one embodiment, the subject has become symptomatic for the ocular disorder. In another embodiment, the subject has 10% or more photoreceptor damage/loss. In another embodiment, the subject has 20% or more photoreceptor damage/loss. In another embodiment, the subject has 30% or more photoreceptor damage/loss. In another embodiment, the subject has 40% or more photoreceptor damage/loss. In another embodiment, the subject has 50% or more photoreceptor damage/loss. In another embodiment, the subject has 60% or more photoreceptor damage/loss. In another embodiment, the subject has 70% or more photoreceptor damage/loss. In another embodiment, the subject has 80% or more photoreceptor damage/loss. In another embodiment, the subject has 90% or more photoreceptor damage/loss. In another embodiment, the subject's bipolar cell circuitry to ganglion cells and optic nerve remains intact.

A. THE AAV CAPSID

A recombinant AAV capsid protein as described herein is characterized by a mutation in aa 587-595 as compared to the wild type full length (vp1) AAV8 capsid sequence, or a mutation in the analogous region of another AAV capsid as compared to the corresponding AAV wild type capsid sequence. An alignment of the amino acid predicted amino acid sequences for capsid protein vp1 of AAV1, -2, -3A, -3B, -4, -6, -7, and -8 is shown in FIG. 1, with a box around the region of mutation of the capsid described herein (Gao G et al. PNAS, September 2002; 99:11854-11859). This region is relatively homologous across AAV serotypes, and corresponds to a region in the capsid protein which is circled in FIG. 2. This loop has been alternatively identified as the HI loop (Nam, H. J. et al (2007) J. Virol. 81: 12260-12271), or the GH loop (Asokan et al, (January 2010), Nat Biotechnol., 28(1): 79-82).

Also encompassed by the invention are nucleic acid sequences encoding the novel AAV, capsids, and fragments thereof which are described herein. In one embodiment, the recombinant AAV capsid protein is characterized by a mutation in nt 1759-1785 of the sequence coding for the AAV8 capsid protein as compared to the AAV8 wild type sequence, or a mutation in the analogous region of the sequence coding for another AAV capsid as compared to the corresponding AAV wild type capsid sequence.

Although, for convenience, reference is made herein to AAV8, it is to be understood that mutations in the homologous region of other AAV serotype capsids are also encompassed by the invention. As used herein, the term "wild type" refers to the native AAV sequence without mutation in aa 587-595 (using AAV8 numbering) of the capsid protein. However it is not intended that only naturally occurring AAV be the source of the wild type sequence. Useful herein are non-naturally occurring AAV, including, without limitation, recombinant, modified or altered, chimeric, hybrid, synthetic, artificial, etc., AAV. This includes AAV with mutations in regions of the capsid other than in aa 587-595, provided they are used as the "starting sequence" for generating the mutant capsid described herein.

The AAV capsid consists of three overlapping coding sequences, which vary in length due to alternative start codon usage. These variable proteins are referred to as VP1, VP2 and VP3, with VP1 being the longest and VP3 being the shortest. The AAV particle consists of all three capsid proteins at a ratio of ~1:1:10 (VP1:VP2:VP3). VP3, which is comprised in VP1 and VP2 at the N-terminus, is the main structural component that builds the particle. The capsid protein can be referred to using several different numbering systems. For convenience, as used herein, the AAV sequences are referred to using VP1 numbering, which starts with aa 1 for the first residue of VP1. However, the capsid proteins described herein include VP1, VP2 and VP3 (used interchangeably herein with vp1, vp2 and vp3) with mutations in the corresponding region of the protein. In AAV8, the variable proteins correspond to VP1 (aa 1 to 738), VP2 (aa 138 to 738), and VP3 (aa 203 to 738) using the numbering of the full length VP1. For clarity, when referring to the mutation, it is meant aa 587-595 of the VP1, aa 450-458 of the VP2, and aa 385-393 of the VP3 of AAV8, if using the first amino acid of the particular vp capsid sequence as aa 1.

In one embodiment, AAV8 is the wild type sequence used when generating the mutant. The amino acid sequence of wild type AAV8 is shown as SEQ ID NO: 8. In one embodiment, the wild type sequence is SEQ ID NO: 8. In other embodiments any other AAV serotype is useful as the starting wild type sequence. In another embodiment, the AAV wild type sequence is a Clade E AAV. A clade is a group of AAV which are phylogenetically related to one another as determined using a Neighbor-Joining algorithm by a bootstrap value of at least 75% (of at least 1000 replicates) and a Poisson correction distance measurement of no more than 0.05, based on alignment of the AAV vp1 amino acid sequence. The Neighbor-Joining algorithm has been described extensively in the literature. See, e.g., M. Nei and S. Kumar, Molecular Evolution and Phylogenetics (Oxford University Press, New York (2000).

Clade E is characterized by containing the previously described AAV8 (G. Gao et al, PNAS, September 2002), 43.1/rh.2; 44.2/rh.10; rh. 25; 29.3/bb.1; and 29.5/bb.2 [US Patent Publication No. US 2003/0138772 A1 (Jul. 24, 2003)]. Additional clade E sequences are described in U.S. Pat. No. 7,096,111, which is incorporated herein by reference. Other AAV which are useful as wild type sequences include, without limitation, including, e.g., pi.1, pi.2, pi.3, rh.38; rh.40; rh.43; rh.49; rh.50, rh.51; rh.52; rh.53; rh.57; rh.58; rh.61; rh.64; hu.6; hu.17; hu.37; hu.39; hu. 40; hu.41; hu.42; hu. 66; and hu.67. Still other AAV which are useful as wild type sequences include AAV1, AAV2, AAV3, AAV4, AAV5, AAV6, AAV7, and AAV9.

AAV-b

Of the many cell types in the retina, the bipolar cells are the least amenable to transduction by AAV. This may be due to a lack of appropriate receptor expression on the cell surface to mediate uptake, or to intrinsic factors governing viral trafficking and processing in the cell. Not wishing to be bound by theory, the inventors assumed that the lack of AAV-mediated expression in the bipolar cells is largely due to failure of the capsid to bind and transduce this cell rather than to features of the cell machinery that might inhibit expression from the viral genome. When injected subretinally AAV2/8 is shown to penetrate deeper into the retinal layers compared to other serotypes (Vandenberghe et al., 2011), therefore as it already offered potential to 'reach' the bipolar cell layer the AAV8 capsid was chosen as the template for modification. A 9 amino acid stretch of a conformationally variable region of AAV8 capsid from 585-594 was specifically selected for potential to alter receptor attachment and cellular transduction properties of the virus. This was based on information from 3D models and targeted mutagenesis studies of the capsid (Gurda et al., 2012; Nam et al., 2007; Padron et al., 2005; Xie et al., 2002) (FIG. 2). The AAV shell is assembled from 60 copies of viral proteins (VP), VP1 (87 kDa), VP2 (73 kDa), and VP3 (61 kDa). The conserved core of each VP subunit consists of an eight-stranded, β-barrel motif and an α-helix (Xie et al., 2002). The outer surface of the capsid is formed by large loops that connect the strands of the β-barrel. For example, the residues from amino acid 585-594 encompass finger-like loops in one VP subunit. The amino acid sequences and structural topology of these loops are reported to facilitate tissue tropism and transduction efficiency (Agbandje-McKenna and Kleinschmidt, 2011). Furthermore, these residues contribute to the top of the protrusions that surround the icosahedral 3-fold axes, formed through symmetric interactions between the VPs. Thus this sequence holds a prominent position on the capsid. This region includes sites shown in some serotypes (notably AAV2) to be critical for heparan-sulfate-binding and cellular uptake (Kern et al., 2003; Opie et al., 2003). The residues are not conserved in the AAV8 capsid suggestive of the fact that AAV8 does not show affinity for heparan-sulfate (Wobus et al, 2000, Wu et al, 2006). Furthermore, an analogous domain was previously interchanged between AAV serotypes and shown to alter tropism profiles dramatically (Asokan et al., 2010). It is possible that this region in AAV8 is less subject to the evolutionary pressure that would prevent alternative capsid formation in other serotypes, while nonetheless producing a surface-exposed epitope that may influence tissue tropism and transduction characteristics.

As shown in the examples below, the inventors have shown that the AAV termed AAV-b effectively transduces bipolar, ganglion, and other ocular cells. In addition, a primary benefit of AAV-b is its strength. Injection of AAV-b results in efficient and early onset transduction of cone photoreceptors, inner retinal cells and ganglion cells. It was noted that AAV8-b targets cone photoreceptors and bipolar cells extremely efficiently. In addition, AAV-b is able to transduce these cells using a relatively low titer of virus. A further recognized benefit of AAV-b is the early onset of gene expression in some tissues.

AAV-b comprises the amino acid sequence of Pro-Glu-Arg-Thr-Ala-Met-Ser-Leu-Pro (SEQ ID NO: 1) at amino acid positions 587-595. In one embodiment, a capsid comprising SEQ ID NO: 1 is provided. In another embodiment, the capsid protein comprises SEQ ID NO: 1 at aa 587-595 of the AAV8 capsid protein or at a corresponding region of another AAV capsid sequence. In another embodiment, the capsid protein comprises the amino acid sequence of SEQ ID NO: 3. In this embodiment, the capsid sequence is referred to as AAV-8b. In other embodiments, the capsid sequence is derived from another wild type sequence, but replaces the sequence at the corresponding region of aa 587-595 with SEQ ID NO: 1.

In another embodiment, nucleic acid sequences encoding the AAV-b viruses, capsids and fragments described herein are provided. In one embodiment, a polynucleotide is provided comprising the sequence nt 1759-CCT GAG CGG ACG GCG ATG AGT CTT CCG-1785 (SEQ ID NO: 9). In one embodiment, a nucleic acid sequence comprising SEQ ID NO: 9 is provided. In another embodiment, a nucleic acid sequence encoding a capsid protein is provided, comprising the sequence SEQ ID NO: 9 at nt 1759-1785 of the sequence encoding the wild type AAV8, or at a corresponding region of another sequence encoding another AAV capsid. In another embodiment, the sequence encoding the capsid protein is SEQ ID NO: 5. In this embodiment, the capsid sequence is referred to as AAV-8b.

AAV-h

As shown in the examples herein, the inventors have shown that the AAV termed AAV-h effectively transduces horizontal, and other, ocular cells. AAV-h has an amino acid sequence of 587-Ser-Phe-Ser-Arg-Ala-Val-Leu-Cys-Asp-595 (SEQ ID NO: 2). In one embodiment, a capsid comprising SEQ ID NO: 2 is provided. In another embodiment, the capsid protein comprises SEQ ID NO: 2 at aa 587-595 of the AAV8 capsid protein or at a corresponding region of another AAV capsid sequence. In another embodiment, the capsid protein has the amino acid sequence of SEQ ID NO: 4. In this embodiment, the capsid sequence is referred to as AAV-8h. In other embodiments, the capsid sequence is derived from another wild type sequence, but replaces the sequence at the corresponding region of aa 587-595 with SEQ ID NO: 2.

In another embodiment, nucleic acid sequences are provided which encode the AAV-h viruses, capsids and fragments described herein. In one embodiment, a polynucleotide comprising the sequence nt 1759-AGT TTT AGT CGT GCG GTT CTT TGT GAT-1785 (SEQ ID NO: 10) is provided. In one embodiment, a nucleic acid sequence comprising SEQ ID NO: 10 is provided. In another embodiment, a nucleic acid sequence encoding a capsid protein is provided, comprising the sequence SEQ ID NO: 10 at nt 1759-1785 of the sequence encoding the wild type AAV8, or at a corresponding region of another sequence encoding another AAV capsid. In another embodiment, the sequence encoding the capsid protein is SEQ ID NO: 6. In this embodiment, the capsid sequence is referred to as AAV-8h.

B. RAAV VECTORS AND COMPOSITIONS

In another aspect, described herein are molecules which utilize the AAV sequences described herein, including fragments thereof, for production of viral vectors useful in delivery of a heterologous gene or other nucleic acid sequences to a target cell. In one embodiment, the vectors useful in compositions and methods described herein contain, at a minimum, sequences encoding a selected AAV capsid as described herein, e.g., an AAVb or AAVh capsid, or a fragment thereof. In another embodiment, useful vectors contain, at a minimum, sequences encoding a selected AAV serotype rep protein, e.g., AAV8 rep protein, or a fragment thereof. Optionally, such vectors may contain both AAV cap and rep proteins. In vectors in which both AAV rep and cap are provided, the AAV rep and AAV cap sequences can both be of one serotype origin, e.g., all AAV8 origin. Alternatively, vectors may be used in which the rep sequences are from an AAV which differs from the wild type AAV providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 described in U.S. Pat. No. 7,282,199, which is incorporated by reference herein. Optionally, the vectors further contain a minigene comprising a selected transgene which is flanked by AAV 5' ITR and AAV 3' ITR. In another embodiment, the AAV is a self-complementary AAV (sc-AAV) (See, US 2012/0141422 which is incorporated herein by reference). Self-complementary vectors package an inverted repeat genome that can fold into dsDNA without the requirement for DNA synthesis or base-pairing between multiple vector genomes. Because scAAV have no need to convert the single-stranded DNA (ssDNA) genome into double-stranded DNA (dsDNA) prior to expression, they are more efficient vectors. However, the trade-off for this efficiency is the loss of half the coding capacity of the vector, ScAAV are useful for small protein-coding genes (up to ~55 kd) and any currently available RNA-based therapy.

In one aspect, the vectors described herein contain nucleic acid sequences encoding an intact AAV capsid as described herein. In one embodiment, the capsid comprises amino acids 1 to 738 of SEQ ID NO: 3 or 4. In another embodiment, the AAV has a recombinant AAV capsid comprising a mutation in aa 587-595 of the AAV8 capsid protein sequence as compared to the AAV8 wild type capsid sequence or a mutation in a corresponding region of another AAV capsid protein as compared to the corresponding wild type capsid sequence. In another embodiment, the AAV capsid comprises the sequence of SEQ ID NO: 1 or SEQ ID NO: 2. In another embodiment, the capsid is encoded by the sequence of SEQ ID NO: 5 or SEQ ID NO: 6. In another embodiment, the a rAAV may have a capsid protein comprising one or more of the capsid regions selected from the vp2 and/or vp3, or from vp1, as described above.

Pseudotyped vectors, wherein the capsid of one AAV is replaced with a heterologous capsid protein, are useful herein. For illustrative purposes, AAV2/8-b (or AAV2/8-h) is used in the examples described below. See, Mussolino et al, cited above. Unless otherwise specified, the AAV ITRs, and other selected AAV components described herein, may be individually selected from among any AAV serotype, including, without limitation, AAV1, AAV2, AAV3, AAV4, AAV5, AAV6, AAV7, AAV8, AAV9 or other known and unknown AAV serotypes. In one desirable embodiment, the ITRs of AAV serotype 2 are used. However, ITRs from other suitable serotypes may be selected. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like. In one embodiment, the AAV comprises the sequence of SEQ ID NO: 5, which corresponds to the full length DNA sequence of AAV8-b. In another embodiment, the AAV comprises the sequence of SEQ ID NO: 6, which corresponds to the full length DNA sequence of AAV8-h.

The rAAV described herein also comprise a minigene. The minigene is composed of, at a minimum, a heterologous nucleic acid sequence (the transgene), as described below, and its regulatory sequences, and 5' and 3' AAV inverted terminal repeats (ITRs). It is this minigene which is packaged into a capsid protein and delivered to a selected target cell.

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a target cell. The heterologous nucleic acid sequence (transgene) can be derived from any organism. The AAV may comprise one or more transgenes.

The composition of the transgene sequence will depend upon the use to which the resulting vector will be put. In one desirable embodiment, the transgene is selected to provide optogenetic therapy. In optogenetic therapy, artificial photoreceptors are constructed by gene delivery of light-activated channels or pumps to surviving cell types in the remaining retinal circuit. This is particularly useful for patients who have lost a significant amount of photoreceptor function, but whose bipolar cell circuitry to ganglion cells and optic nerve remains intact. In one embodiment, the heterologous nucleic acid sequence (transgene) is an opsin. The opsin sequence can be derived from any suitable single- or multicellular-organism, including human, algae and bacteria. In one embodiment, the opsin is rhodopsin, photopsin, L/M wavelength (red/green)-opsin, or short wavelength (S) opsin (blue). In another embodiment, the opsin is channel-rhodopsin or halorhodopsin.

In another embodiment, the transgene is selected for use in gene augmentation therapy, i.e., to provide replacement copy of a gene that is missing or defective. In this embodiment, the transgene may be readily selected by one of skill in the art to provide the necessary replacement gene. In one embodiment, the missing/defective gene is related to an ocular disorder. In another embodiment, the transgene is NYX, GRM6, TRPM1L or GPR179 and the ocular disorder is Congenital Stationary Night Blindness. See, e.g., Zeitz et al, Am J Hum Genet. 2013 Jan. 10; 92(1):67-75. Epub 2012 Dec. 13 which is incorporated herein by reference.

In another embodiment, the transgene is selected for use in gene suppression therapy, i.e., expression of one or more native genes is interrupted or suppressed at transcriptional or translational levels. This can be accomplished using short hairpin RNA (shRNA) or other techniques well known in the art. See, e.g., Sun et al, Int J Cancer. 2010 Feb. 1; 126(3): 764-74 and O'Reilly M, et al. Am J Hum Genet. 2007 July; 81(1):127-35, which are incorporated herein by reference. In this embodiment, the transgene may be readily selected by one of skill in the art based upon the gene which is desired to be silenced.

In another embodiment, the transgene comprises more than one transgene. This may be accomplished using a single vector carrying two or more heterologous sequences, or using two or more AAV each carrying one or more heterologous sequences. In one embodiment, the AAV is used for gene suppression (or knockdown) and gene augmentation co-therapy. In knockdown/augmentation co-therapy, the defective copy of the gene of interest is silenced and a non-mutated copy is supplied. In one embodiment, this is accomplished using two or more co-administered vectors. See, Millington-Ward et al, Molecular Therapy, April 2011, 19(4):642-649 which is incorporated herein by reference.

The transgenes may be readily selected by one of skill in the art based on the desired result.

In another embodiment, the transgene is selected for use in gene correction therapy. This may be accomplished using, e.g., a zinc-finger nuclease (ZFN)-induced DNA double-strand break in conjunction with an exogenous DNA donor substrate. See, e.g., Ellis et al, Gene Therapy (epub January 2012) 20:35-42 which is incorporated herein by reference. The transgenes may be readily selected by one of skill in the art based on the desired result.

In another embodiment, the transgene is selected for use in neurotropic factor gene therapy, i.e., providing exogenous neurotropic factors to provide neuroprotection. In this embodiment, the transgene may be any neurotropic factor, including ciliary-derived neurotrophic factor (CNTF), fibroblast growth factor (FGF), glial-derived neurotrophic factor (GDNF), Rod-derived Cone Viability Factor (RdCVF) (Yang et al, Mol Ther. 2009 May; 17(5):787-95) and brain-derived neurotrophic factor (BDNF). See, e.g., Schlichtenbrede et al, Gene Therapy (2003) 10, 523-527. The neurotropic factor may be readily selected by one of skill in the art. These documents are incorporated herein by reference.

In another embodiment, the transgenes useful herein include reporter sequences, which upon expression produce a detectable signal. Such reporter sequences include, without limitation, DNA sequences encoding β-lactamase, β-galactosidase (LacZ), alkaline phosphatase, thymidine kinase, green fluorescent protein (GFP), red fluorescent protein (RFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (MA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

Desirably, the transgene encodes a product which is useful in biology and medicine, such as proteins, peptides, RNA, enzymes, or catalytic RNAs. Desirable RNA molecules include shRNA, tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used to correct or ameliorate gene deficiencies (as in the applications discussed above), which may include deficiencies in which normal genes are expressed at less than normal levels or deficiencies in which the functional gene product is not expressed. A preferred type of transgene sequence encodes a therapeutic protein or polypeptide which is expressed in a target cell. The invention further includes using multiple transgenes, e.g., to correct or ameliorate a gene defect caused by a multi-subunit protein. In certain situations, a different transgene may be used to encode each subunit of a protein, or to encode different peptides or proteins. This is desirable when the size of the DNA encoding the protein subunit is large. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, J. Gen. Virol., 78(Pt 1):13-21 (January 1997); Furler, S., et al, Gene Ther., 8(11):864-873 (June 2001); Klump H., et al., Gene Ther., 8(10):811-817 (May 2001). This 2A peptide is significantly smaller than an IRES, making it well suited for use when space is a limiting factor. However, the selected transgene may encode any biologically active product or other product, e.g., a product desirable for study.

The regulatory sequences include conventional control elements which are operably linked to the transgene in a manner which permits its transcription, translation and/or expression in a cell transfected with the vector or infected with the virus produced as described herein. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters, are known in the art and may be utilized.

The regulatory sequences useful in the constructs provided herein may also contain an intron, desirably located between the promoter/enhancer sequence and the gene. One desirable intron sequence is derived from SV-40, and is a 100 bp mini-intron splice donor/splice acceptor referred to as SD-SA. Another suitable sequence includes the woodchuck hepatitis virus post-transcriptional element. (See, e.g., L. Wang and I. Verma, 1999 Proc. Natl. Acad. Sci., USA, 96:3906-3910). PolyA signals may be derived from many suitable species, including, without limitation SV-40, human and bovine.

Another regulatory component of the rAAV useful in the methods described herein is an internal ribosome entry site (IRES). An IRES sequence, or other suitable systems, may be used to produce more than one polypeptide from a single gene transcript. An IRES (or other suitable sequence) is used to produce a protein that contains more than one polypeptide chain or to express two different proteins from or within the same cell. An exemplary IRES is the poliovirus internal ribosome entry sequence, which supports transgene expression in photoreceptors, RPE and ganglion cells. Preferably, the IRES is located 3' to the transgene in the rAAV vector.

In one embodiment, the AAV comprises a promoter (or a functional fragment of a promoter). The selection of the promoter to be employed in the rAAV may be made from among a wide number of constitutive or inducible promoters that can express the selected transgene in the desired target cell. In one embodiment, the target cell is an ocular cell. The promoter may be derived from any species, including human. Desirably, in one embodiment, the promoter is "cell specific". The term "cell-specific" means that the particular promoter selected for the recombinant vector can direct expression of the selected transgene in a particular cell or ocular cell type. In one embodiment, the promoter is specific for expression of the transgene in photoreceptor cells. In another embodiment, the promoter is specific for expression in the rods and/or cones. In another embodiment, the promoter is specific for expression of the transgene in RPE cells. In another embodiment, the promoter is specific for expression of the transgene in ganglion cells. In another embodiment, the promoter is specific for expression of the transgene in Mueller cells. In another embodiment, the promoter is specific for expression of the transgene in bipolar cells. In another embodiment, the promoter is specific for expression of the transgene in ON-bipolar cells. In one embodiment, the promoter is metabotropic glutamate receptor 6 (mGluR6) promoter (see, Vardi et al, mGluR6 Transcripts in Non-neuronal Tissues, J Histochem Cytochem. 2011 December; 59(12): 1076-1086, which is incorporated herein by reference). In another embodiment, the promoter is an enhancer-linked mGluR6 promoter. In another embodiment, the promoter is specific for expression of the transgene in OFF-bipolar cells. In another embodiment, the promoter is specific for expression of the transgene in horizontal cells. In another embodiment, the promoter is specific for expression of the transgene in amacrine cells. In another embodiment, the transgene is expressed in any of the above noted ocular cells.

In another embodiment, promoter is the native promoter for the gene to be expressed. Useful promoters include, without limitation, the rod opsin promoter, the red-green opsin promoter, the blue opsin promoter, the cGMP-β-phosphodiesterase promoter, the mouse opsin promoter (Beltran et al 2010 cited above), the rhodopsin promoter (Mussolino et al, Gene Ther, July 2011, 18(7):637-45); the alpha-subunit of cone transducin (Morrissey et al, BMC Dev, Biol, January 2011, 11:3); beta phosphodiesterase (PDE) promoter; the retinitis pigmentosa (RP1) promoter (Nicord et al, J. Gene Med, December 2007, 9(12):1015-23); the NXNL2/NXNL1 promoter (Lambard et al, PLoS One, October 2010, 5(10):e13025), the RPE65 promoter; the retinal degeneration slow/peripherin 2 (Rds/perph2) promoter (Cai et al, Exp Eye Res. 2010 August; 91(2):186-94); and the VMD2 promoter (Kachi et al, Human Gene Therapy, 2009 (20:31-9)). Each of these documents is incorporated by reference herein.

Other useful promoters include transcription factor promoters including, without limitation, promoters for the neural retina leucine zipper (Nrl), photoreceptor-specific nuclear receptor Nr2e3, and basic-leucine zipper (bZIP). In one embodiment, the promoter is of a small size, under 1000 bp, due to the size limitations of the AAV vector. In another embodiment, the promoter is under 400 bp.

Other promoters useful herein include ubiquitous or constitutive promoters, when universal expression of the transgene is desired. In one embodiment, the promoter is selected from the human EF1a promoter, phosphoglycerate kinase-1 (PGK) promoter, and cytomegalovirus (CMV) promoter (optionally with the CMV enhancer). Other examples of constitutive promoters useful herein include, without limitation, the retroviral Rous sarcoma virus (RSV) LTR promoter (optionally with the RSV enhancer), the SV40 promoter, the dihydrofolate reductase promoter, the chicken β-actin (CBA) promoter, and the immediate early CMV enhancer coupled with the CBA promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. In one embodiment, the inducible promoter is selected from rapamycin/rapalog promoter, the ecdysone promoter, the estrogen-responsive promoter, and the tetracycline-responsive promoter. Examples of other inducible promoters regulated by exogenously supplied compounds which are useful herein, include, the zinc-inducible sheep metallothionine (MT) promoter, the dexamethasone (Dex)-inducible mouse mammary tumor virus (MMTV) promoter, the T7 polymerase promoter system. Other types of inducible promoters which may be useful in this context are those which are regulated by a specific physiological state, e.g., temperature, acute phase, a particular differentiation state of the cell, or in replicating cells only. In one embodiment, any type of inducible promoter which is tightly regulated and is specific for the particular target ocular cell type may be used.

Other regulatory sequences useful herein include enhancer sequences. Enhancer sequences useful herein include the IRBP enhancer (Nicord 2007, cited above), immediate early cytomegalovirus enhancer, one derived from an immunoglobulin gene or SV40 enhancer, the cis-acting element identified in the mouse proximal promoter, etc.

Selection of these and other common vector and regulatory elements are conventional and many such sequences are available. See, e.g., Sambrook et al, and references cited therein at, for example, pages 3.18-3.26 and 16.17-16.27 and Ausubel et al., Current Protocols in Molecular Biology, John Wiley & Sons, New York, 1989). Of course, not all vectors and expression control sequences will function equally well to express all of the transgenes as described herein. However, one of skill in the art may make a selection among these, and other, expression control sequences without departing from the scope of this invention.

In another embodiment, a method of generating a recombinant adeno-associated virus is provided. A suitable recombinant adeno-associated virus (AAV) is generated by culturing a host cell which contains a nucleic acid sequence encoding an AAV capsid protein as described herein, or fragment thereof; a functional rep gene; a minigene composed of, at a minimum, AAV inverted terminal repeats (ITRs) and a heterologous nucleic acid sequence encoding a desirable transgene; and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

Most suitably, such a stable host cell will contain the required component(s) under the control of an inducible promoter. However, the required component(s) may be under the control of a constitutive promoter. Examples of suitable inducible and constitutive promoters are provided herein, in the discussion below of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV described herein may be delivered to the packaging host cell in the form of any genetic element which transfers the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, 1993 *J. Virol.*, 70:520-532 and U.S. Pat. No. 5,478,745, among others. These publications are incorporated by reference herein.

C. PHARMACEUTICAL COMPOSITIONS AND ADMINISTRATION

In one embodiment, the recombinant AAV containing the desired transgene and cell-specific promoter for use in the target ocular cells as detailed above is optionally assessed for contamination by conventional methods and then formulated into a pharmaceutical composition intended for subretinal or intravitreal injection. Such formulation involves the use of a pharmaceutically and/or physiologically acceptable vehicle or carrier, particularly one suitable for administration to the eye, e.g., by subretinal injection, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. Publication No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20. In another embodiment, the pharmaceutically acceptable carrier comprises a surfactant, such as perfluorooctane (Perfluoron liquid).

In certain embodiments of the methods described herein, the pharmaceutical composition described above is administered to the subject by subretinal injection. In other embodiments, the pharmaceutical composition is administered by intravitreal injection. Other forms of administration that may be useful in the methods described herein include, but are not limited to, direct delivery to a desired organ (e.g., the eye), oral, inhalation, intranasal, intratracheal, intravenous, intramuscular, subcutaneous, intradermal, and other parental routes of administration. Routes of administration may be combined, if desired.

Furthermore, in certain embodiments it is desirable to perform non-invasive retinal imaging and functional studies to identify areas of specific ocular cells to be targeted for therapy. In these embodiments, clinical diagnostic tests are employed to determine the precise location(s) for one or more subretinal injection(s). These tests may include ophthalmoscopy, electroretinography (ERG) (particularly the b-wave measurement), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, etc. These, and other desirable tests, are described in International Patent Application No. PCT/US2013/022628. In view of the imaging and functional studies, in some embodiments, one or more injections are performed in the same eye in order to target different areas of retained bipolar cells. The volume and viral titer of each injection is determined individually, as further described below, and may be the same or different from other injections performed in the same, or contralateral, eye. In another embodiment, a single, larger volume injection is made in order to treat the entire eye. In one embodiment, the volume and concentration of the rAAV composition is selected so that only a specific region of ocular cells is impacted. In another embodiment, the volume and/or concentration of the rAAV composition is a greater amount, in order reach larger portions of the eye, including non-damaged ocular cells.

The composition may be delivered in a volume of from about 0.1 µL to about 1 mL, including all numbers within the range, depending on the size of the area to be treated, the viral titer used, the route of administration, and the desired effect of the method. In one embodiment, the volume is about 50 µL. In another embodiment, the volume is about 70 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 250 µL. In another embodiment, the volume is about 300 µL. In another embodiment, the volume is about 450 µL. In another embodiment, the volume is about 500 µL. In another embodiment, the volume is about 600 µL. In another embodiment, the volume is about 750 µL. In another embodiment, the volume is about 850 µL. In another embodiment, the volume is about 1000 µL. An effective concentration of a recombinant adeno-associated virus carrying a nucleic acid sequence encoding the desired transgene under the control of the cell-specific promoter sequence desirably ranges from about $10^7$ and $10^{13}$ vector genomes per milliliter (vg/mL) (also called genome copies/mL (GC/mL)). The rAAV infectious units are measured as described in S. K. McLaughlin et al, 1988 J. Virol., 62:1963, which is incorporated herein by reference. Preferably, the concentration in the retina is from about $1.5 \times 10^9$ vg/mL to about $1.5 \times 10^{12}$ vg/mL, and more preferably from about $1.5 \times 10^9$ vg/mL to about $1.5 \times 10^{11}$ vg/mL. In one embodiment, the effective concentration is about $1.4 \times 10^8$ vg/mL. In one embodiment, the effective concentration is about $3.5 \times 10^{10}$ vg/mL. In another embodiment, the effective concentration is about $5.6 \times 10^{11}$ vg/mL. In another embodiment, the effective concentration is about $5.3 \times 10^{12}$ vg/mL. In yet another embodiment, the effective concentration is about $1.5 \times 10^{12}$ vg/mL. In another embodiment, the effective concentration is about $1.5 \times 10^{13}$ vg/mL. In one embodiment, the effective dosage (total genome copies delivered) is from about $10^7$ to $10^{13}$ vector genomes. It is desirable that the lowest effective concentration of virus be utilized in order to reduce the risk of undesirable effects, such as toxicity, retinal dysplasia and detachment. Still other dosages and administration volumes in these ranges may be selected by the attending physician, taking into account the physical state of the subject, preferably human, being treated, the age of the subject, the particular ocular disorder and the degree to which the disorder, if progressive, has developed. For extra-ocular delivery, the dosage will be increased according to the scale-up from the retina. Intravenous delivery, for example may require doses on the order of $1.5 \times 10^{13}$ vg/kg.

D. METHODS OF TREATMENT/PROPHYLAXIS

Described herein are various methods of preventing, treating, arresting progression of or ameliorating the above-described ocular disorders and retinal changes associated therewith. Generally, the methods include administering to a mammalian subject in need thereof, an effective amount of a composition comprising a recombinant adeno-associated virus (AAV) described above, carrying a nucleic acid sequence encoding transgene, or fragment thereof, under the control of regulatory sequences which express the product of the gene in the subject's ocular cells, and a pharmaceutically acceptable carrier. Any of the AAV described herein are useful in the methods described below.

The retinal diseases described above are associated with various retinal changes. These may include a loss of photoreceptor structure or function; thinning or thickening of the outer nuclear layer (ONL); thinning or thickening of the outer plexiform layer (OPL); disorganization followed by loss of rod and cone outer segments; shortening of the rod and cone inner segments; retraction of bipolar cell dendrites; thinning or thickening of the inner retinal layers including inner nuclear layer, inner plexiform layer, ganglion cell layer and nerve fiber layer; opsin mislocalization; overexpression of neurofilaments; thinning of specific portions of the retina (such as the fovea or macula); loss of ERG function; loss of visual acuity and contrast sensitivity; loss of optokinetic reflexes; loss of the pupillary light reflex; and loss of visually guided behavior. In one embodiment, a method of preventing, arresting progression of or ameliorating any of the retinal changes associated with these retinal diseases is provided. As a result, the subject's vision is improved, or vision loss is arrested and/or ameliorated.

In a particular embodiment, a method of preventing, arresting progression of or ameliorating vision loss associated with an ocular disorder in the subject is provided. Vision loss associated with an ocular disorder refers to any decrease in peripheral vision, central (reading) vision, night vision, day vision, loss of color perception, loss of contrast sensitivity, or reduction in visual acuity.

In another embodiment, a method of targeting one or more ocular cells for optogenetic therapy in a subject in need thereof is provided. As discussed above, optogenetic therapy is a method of providing "substitute" photoreceptor function in subjects who have significant photoreceptor damage. In one embodiment, the cells targeted for optogenetic therapy are bipolar cells. In another embodiment, the cells targeted for optogenetic therapy are ganglion cells. In another embodiment, all ocular cells are targeted.

In another embodiment, a method of targeting one or more type(s) of ocular cells for gene augmentation therapy in a subject in need thereof is provided. In another embodiment, a method of targeting one or more type of ocular cells for gene suppression therapy in a subject in need thereof is provided. In yet another embodiment, a method of targeting one or more type of ocular cells for gene knockdown/augmentation therapy in a subject in need thereof is provided. In another embodiment, a method of targeting one or more type of ocular cells for gene correction therapy in a subject in need thereof is provided. In still another embodiment, a method of targeting one or more type of ocular cells for neurotropic factor gene therapy in a subject in need thereof is provided.

In any of the methods described herein, the targeted cell may be an ocular cell. In one embodiment, the targeted cell is an RPE cell. In another embodiment, the targeted cell is a photoreceptor. In another embodiment, the photoreceptor is a cone cell. In another embodiment, the targeted cell is a Mueller cell. In another embodiment, the targeted cell is a bipolar cell. In yet another embodiment, the targeted cell is a horizontal cell. In another embodiment, the targeted cell is an amacrine cell. In still another embodiment, the targeted cell is a ganglion cell. In still another embodiment, the gene may be expressed and delivered to an intracellular organelle, such as a mitochondrion or a lysosome.

As used herein "photoreceptor function loss" means a decrease in photoreceptor function as compared to a normal, non-diseased eye or the same eye at an earlier time point. As used herein, "increase photoreceptor function" means to improve the function of the photoreceptors or increase the number or percentage of functional photoreceptors as compared to a diseased eye (having the same ocular disease), the same eye at an earlier time point, a non-treated portion of the same eye, or the contralateral eye of the same patient. Photoreceptor function may be assessed using the functional studies described above and in the examples below, e.g., ERG or perimetry, which are conventional in the art.

For each of the described methods, the treatment may be used to prevent the occurrence of retinal damage or to rescue eyes having mild or advanced disease. As used herein, the term "rescue" means to prevent progression of the disease to total blindness, prevent spread of damage to uninjured ocular cells, improve damage in injured ocular cells, or to provide enhanced vision. In one embodiment, the composition is administered before the disease becomes symptomatic or prior to photoreceptor loss. By symptomatic is meant onset of any of the various retinal changes described above or vision loss. In another embodiment, the composition is administered after disease becomes symptomatic. In yet another embodiment, the composition is administered after initiation of photoreceptor loss. In another embodiment, the composition is administered after outer nuclear layer (ONL) degeneration begins. In some embodiments, it is desirable that the composition is administered while bipolar cell circuitry to ganglion cells and optic nerve remains intact. In one embodiment, the bipolar cells are targeted for optogenetic therapy. By ensuring that the composition is administered while the circuitry to ganglion cells and optic nerve remains intact, it is possible to provide "substitute" photoreceptor cells, and increase vision.

In another embodiment, the composition is administered after initiation of photoreceptor loss. In yet another embodiment, the composition is administered when less than 90% of the photoreceptors are functioning or remaining, as compared to a non-diseased eye. In another embodiment, the composition is administered when less than 80% of the photoreceptors are functioning or remaining. In another embodiment, the composition is administered when less than 70% of the photoreceptors are functioning or remaining. In another embodiment, the composition is administered when less than 60% of the photoreceptors are functioning or remaining. In another embodiment, the composition is administered when less than 50% of the photoreceptors are functioning or remaining. In another embodiment, the composition is administered when less than 40% of the photoreceptors are functioning or remaining. In another embodiment, the composition is administered when less than 30% of the photoreceptors are functioning or remaining. In another embodiment, the composition is administered when less than 20% of the photoreceptors are functioning or remaining. In another embodiment, the composition is administered when less than 10% of the photoreceptors are functioning or remaining. In one embodiment, the composition is administered only to one or more regions of the eye. In another embodiment, the composition is administered to the entire eye.

In another embodiment, the method includes performing functional and imaging studies to determine the efficacy of the treatment. These studies include ERG and in vivo retinal imaging, as described in the examples below. In addition visual field studies, perimetry and microperimetry, pupillometry, mobility testing, visual acuity, contrast sensitivity, color vision testing may be performed.

In yet another embodiment, any of the above described methods is performed in combination with another, or secondary, therapy. The therapy may be any now known, or as yet unknown, therapy which helps prevent, arrest or ameliorate any of the described retinal changes and/or vision loss. In one embodiment, the secondary therapy is encapsulated cell therapy (such as that delivering Ciliary Neurotrophic Factor (CNTF)). See, Sieving, P. A. et al, 2006. Proc Natl Acad Sci USA, 103(10):3896-3901, which is hereby incorporated by reference. In another embodiment, the secondary therapy is a neurotrophic factor therapy (such as pigment epithelium-derived factor, PEDF; ciliary neurotrophic factor 3; rod-derived cone viability factor (RdCVF) or glial-derived neurotrophic factor). In another embodiment, the secondary therapy is anti-apoptosis therapy (such as that delivering X-linked inhibitor of apoptosis, XIAP). In yet another embodiment, the secondary therapy is rod derived cone viability factor 2. The secondary therapy can be administered before, concurrent with, or after administration of the rAAV described above.

In another embodiment, a method of delivering a transgene to a cell is provided, said method comprising the step of contacting the cell with an AAV described herein, wherein said AAV comprises the minigene.

In another embodiment, a method of delivering a protein to the brain is provided, said method comprising contacting a ganglion cell with an AAV described herein, wherein said AAV comprises the minigene. In one embodiment, the AAV is AAV-b. In another embodiment, the AAV is AAV-8b.

In another embodiment, the use of an AAV or a molecule as described herein is provided in preparing a medicament for delivery of a heterologous nucleic acid molecule encoding the product to a cell. In still another embodiment, a composition is provided comprising an AAV as described herein, for use in treating an ocular condition.

As is demonstrated in the examples below, exemplary AAV-8b and AAV-8h were employed in in vivo experiments to provide evidence of the utility and efficacy of the methods and compositions described herein. The examples demonstrated targeting of ocular cells in mice and dog.

Further, these results show that subretinal injection of AAV8-b in the eye of a large animal model results in efficient and early onset transduction of cone photoreceptors, inner retinal cells and ganglion cells. It was noted that AAV8-b targets cone photoreceptors extremely efficiently. This provides a useful tool for delivering halorhodopsin-mediated optogenetic therapy. In addition, AAV8-b is also useful for treating diseases which originate in cone photoreceptors, such as achromatopsia.

Notably there is little if any transduction of RPE cells with AAV8-b even if the vector is injected subretinally. To the inventors' knowledge, there is no other vector that has this feature. All other AAV serotypes and all of the different pseudotyped lentiviruses which target the eye, target RPE cells efficiently. There is a great need for AAV vectors that do not target RPE cells to treat neural retinal disorders (and not those of the RPE). Further, a lack of transduction of the RPE attenuates side effects/toxicity from targeting of these cells.

In addition, AAV-b targets inner retinal cells efficiently and can be used to deliver optogenetic therapy, including therapy mediated by modified channelopsin proteins. The early onset of expression mediated by this vector allows for rapid reversal of sensorineural deficits.

In addition, AAV-b targets ganglion cells extremely efficiently after either subretinal or intravitreal injection. Thus, this vector may be used through intravitreal injection (an office procedure) to efficiently deliver secretable proteins including, but not limited to, neurotrophic factors, antineovascular factors, molecules that serve as decoy receptors to block function of unwanted proteins. Further, AAV-b, due to its ability to target ganglion cells, is useful in the treatment of glaucoma (a disease which causes loss of ganglion cells).

Further, because AAV-b targets ganglion cells efficiently, this vector may be used to deliver protein to the brain. This approach is useful in developing treatments for degenerative diseases which affect the brain, including lysosomal storage diseases and metabolic diseases.

This data allow one of skill in the art to readily anticipate that these methods may be similarly used in treatment of retinal disease in other subjects, including humans.

E. EXAMPLES

Example 1: Generation of Mutants

Figure 3:
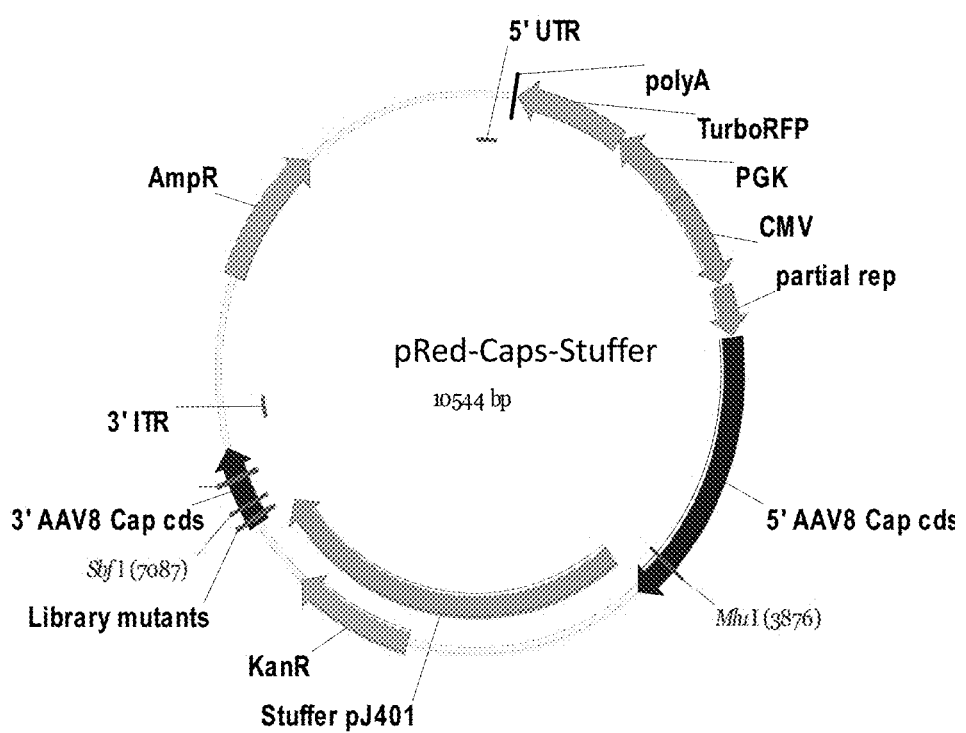
FIG. 3 is a map of the p-Red-Caps-Stuffer plasmid used for production of the library discussed in Example 1.

To find recombinant AAV capable of transducing bipolar cells, the divergent VP3 loop HI of the AAV8 capsid gene was targeted for mutation (FIG. 2). Briefly, a library of mutations across 9 amino acids (aa 587-595 of AAV8 vp1), was engineered into the AAV capsid and this library cloned into the plasmid pRFP-AAV8cap (FIG. 3). The AAV viral library was then produced by triple transfection of 293T cells using standard methods. See, e.g., Flannery and Visel, Methods in Molecular Biology, 935:351-69 (September 2012), which is incorporated by reference herein.

From crystallography studies carried out at 2.6-Å resolution Nam et al have contributed the lack of heparan sulfate binding by AAV8 to be in part due to the structural differences in the region utilized for receptor recognition by AAV2 (highlighted in red in FIG. 1A, from PDB 2QA0, (Nam et al., 2007)). Two critical residues, R585 and R588 are particularly necessary for the ability of AAV2 to bind heparan sulfate (Kern et al., 2003; Opie et al., 2003). These positions align with Q588 and T591, respectively, in AAV8 (Lochrie et al., 2006). Random mutagenesis was carried out on residues from amino acid 585 to 594.

Figure 4:
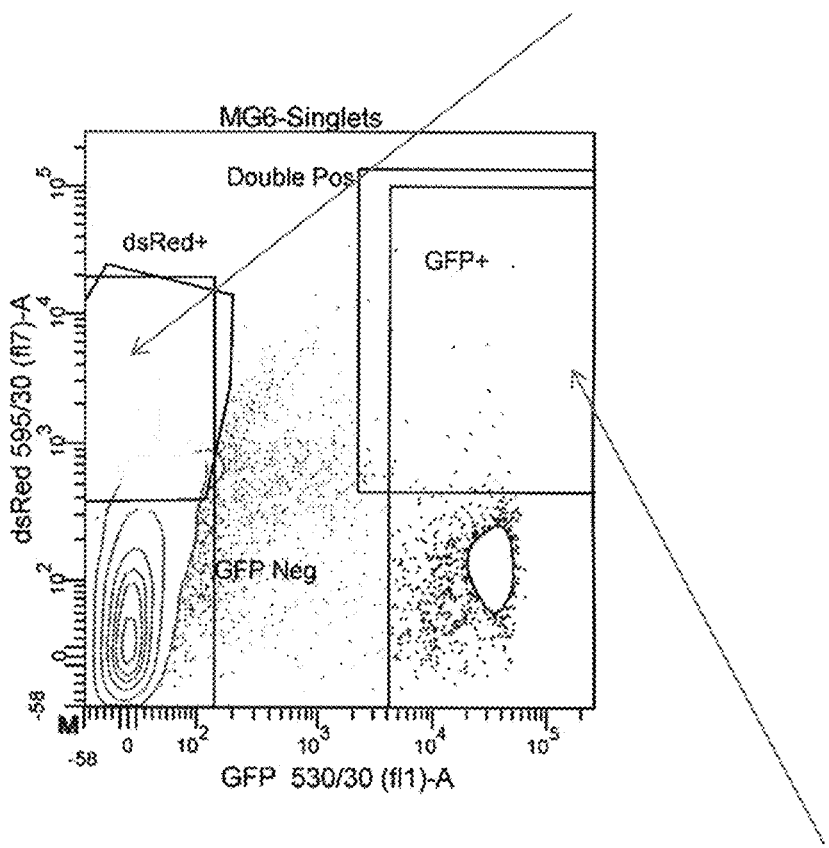
FIG. 4 shows the results of the FACS sorting described in Example 2. The upper right quadrant corresponds to ON-bipolar cells transfected with AAV. The upper left quadrant corresponds to all non-bipolar cells transfected with AAV.

This mutated capsid region was cloned into a vector designed for AAV library production, the red fluorescently labelled plasmid, pAAV8Caps-Lib (FIG. 3). This plasmid which has the AAV2 ITRs flanking the minimal rep/cap gene of AAV8 expressed in reverse orientation to turbo RFP was used to produce the AAV viral library. The plasmid was cotransfected with helper plasmid into 293T cells as described in the methods section. Up to 2 µl of the viral library was subretinally injected into Grm6-EGFP transgenic mice, which have GFP labelling of the ON-bipolar cells. After 3 weeks, cell dissociation and FACS was used to isolate the ON-bipolar cells. These cells included a subset of cells double-labelled with EGFP and dsRED, i.e. library-transfected bipolar cells. The sorted EGFP cells were lysed and the mutant region of the capsid was amplified by PCR and recloned back into the pAAV8Caps-Lib plasmid for a second round of viral library production and injection. It was desirable to select for viruses that could effectively compete with the wild-type capsid. Therefore in the second round, the viral library was spiked with AAV2/8, which in effect served as a negative competing selective force. From this round unmutated and mutant sequences were found in double-positive EGFP/dsRED-labelled cells (transduced ON-bipolar cells) with only unmutated AAV8 capsid sequences isolated from the dsRed-positive, EGFP-negative cells (transduced non-bipolar cells) (FIG. 4). From the double positive red/green cells, the AAVs were isolated and sequenced. Six variants were identified based on their appearance more than once in DNA samples from 50 colonies. These variants were processed for further analysis.

A. Production of Mutated Region by DNA2.0

The region of the AAV8 rep/cap gene between the sbf1 and mlu1 sites was synthesized by the company DNA2.0 (https://www.dna20.com/). This region includes the amino acids 587-595 (counting from the first amino acid of AAV8 vp1) and mutations were incorporated at each position of these 9 amino acids. A combinatorial NNK strategy was used to generate maximum diversity while eliminating two of the three possible stop codons (Muranaka et al, Nucleic Acids Res. 2006 Jan. 5; 34, which is incorporated by reference herein).

B. Cloning of the AAV Plasmid Library:

The plasmid pRed-Caps-Stuffer was linearized with sbf1 and mlu1 (an sbf1 site further upstream was mutated using a site-directed mutagenesis kit prior to cloning to render the extra sbf1 site inactive). We cloned the synthesized mutated region in the sbf1/mlu1 digested backbone using T4 DNA ligase (New England Biolabs). This was electroporated into DH10b electrocompetent bacteria (Invitrogen). It was crucial that no uncut backbone from the WT plasmid escape through the cloning as it would contaminate and saturate the library. The absence of backbone was confirmed by absence of growth on agar-Kanamycin plates.

Up to 20 ul of the transformation broth was plated on agar-Ampicillin plates to estimate the number of transformants. The remainder of the broth was used to inoculate 2 liters of broth to prepare rep/cap plasmid library DNA for AAV production.

C. AAV Library Production

The AAV was prepared according to standard triple transfection protocols with some specifications:

To avoid the packaging of multiple genomes into each capsid a low plasmid concentration was used for the triple transfection—150 ng of rep/cap library plasmid was used per 150 mm confluent HEK293 cell culture plate. By Avogadro's number and the molecular weight of the plasmid it was estimated that 200 DNA capsid molecules were present per HEK293 cell. Ultimately the transfected cell lysates and broths from 70 confluent 150 mm transfected plates were used to prepare the library. This broth and benzonase-treated lysates were concentrated 20-fold using a tangential flow filtration system before virus production according to state of the art.

Example 2: Mutant Selection

The viral library (2 µl) was subretinally injected into 10 adult transgenic mice with GFP-labeled ON-bipolar cells (mGluR6-EGFP mice, as described in Dhingra et al, J Comp Neurol. 2008 Oct. 10; 510(5):484-96 which is incorporated by reference herein). After 3 weeks, the GFP-labeled cells were isolated after retinal cell dissociation FACS sorting. Viruses were isolated from the bipolar cells and the mutant region of the capsid was amplified by PCR and sequenced. These capsid sequences where then reincorporated into the pRFP-AAV8 cap plasmid for a second round of library production and injection.

After 3 weeks, FACS sorting was again performed. ON-bipolar cells expressed a double positive for dsRED and GFP. Non-bipolar cells transfected with AAV were positive for dsRED alone. The ON-bipolar cells accounted for about 1% of the parent population, while the transfected non-bipolars accounted for about 9.1% (FIG. 4). It was noted that a large range of mutants were isolated from both GFP positive cells (bipolar cells) and GFP negative cells (non-bipolar cells) in the first round of selection. Thus, in the second round, the library was spiked with WT AAV8 to serve as a negative competing selective force. From this round mutant sequences were only found in GFP-positive cells (bipolar cells, "double positive" cells) with only WT sequences isolated from the GFP-negative cells.

Figure 6A:
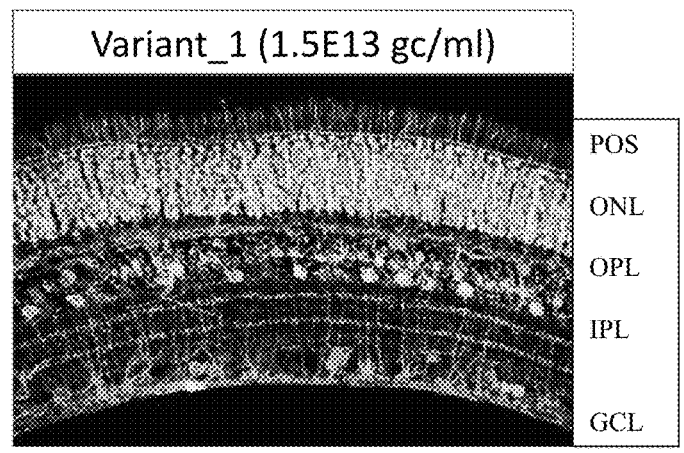
FIG. 6A-E are photographs of 20× images from mouse retinal sections 3 weeks after subretinal injection with selected AAV variants as shown in FIG. 5. These viruses express EGFP under the human EF1alpha promoter (promoter described in J Virol. 2005 March; 79(6):3606-14). Variant 1 shows fluorescence in a diverse range of cell types with the sparsest fluorescence between the outer (OPL) and inner (IPL) plexiform layers where the bipolar cell subtypes are found (FIG. 6A). This layering is identified using a marker for choline acetyl transferase (anti-ChAT). The transduction pattern for variant 1 is qualitatively similar to that seen with the wild-type AAV8 capsid. By contrast strong fluorescence staining is found for variant 2 (AAV8b) in the outer-inner plexiform region (FIG. 6B, shown by an arrow) with many bipolar and amacrine cells stained. Bipolar cell staining is identified here with the marker anti-PKCα. In addition the photoreceptor cell bodies in the outer nuclear layer and their outer segments are strongly stained. The variant 3 virus shows a more distinctive staining pattern with dense staining along the outer plexiform layer with labeling of the horizontal cell bodies and their dense network of spreading dendrites (FIG. 6C, shown by an arrow). The lack of staining in the outer nuclear layer suggests that this variant selects against transduction of the photoreceptor cells. Variant 4 staining is sparse with only a few horizontal and amacrine cells labeled (FIG. 6D). Variant 5 was a negative control (FIG. 6E). POS=Photoreceptor outer segments, ONL=Outer nuclear layer, OPL=outer plexiform layer, IPL=inner plexiform layer, GCL=Ganglion cell layer.
Figure 6B:
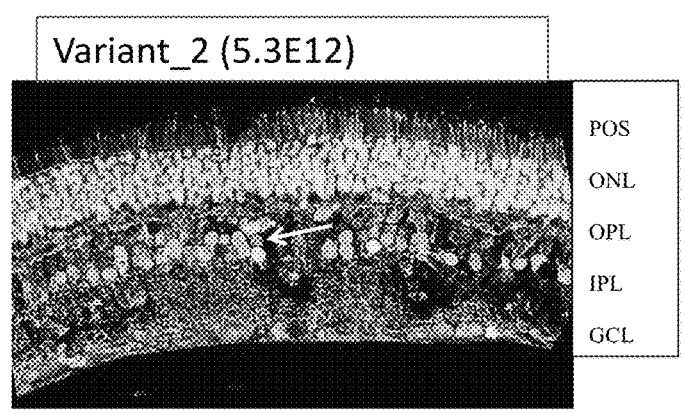
Figure 6C:
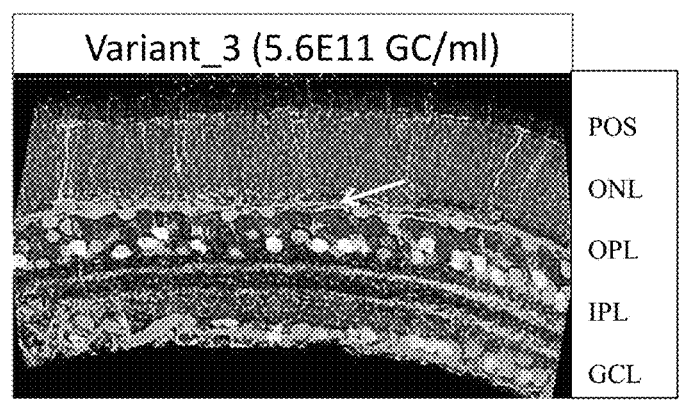
Figure 6D:
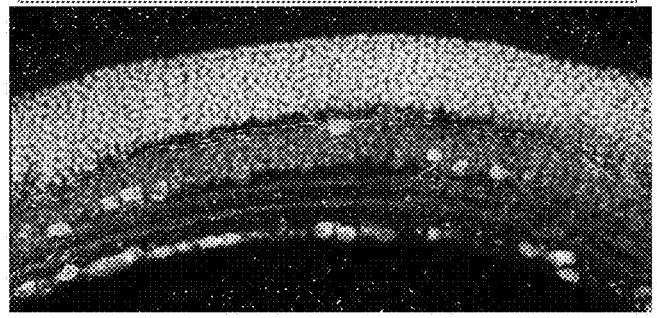
Figure 6E:
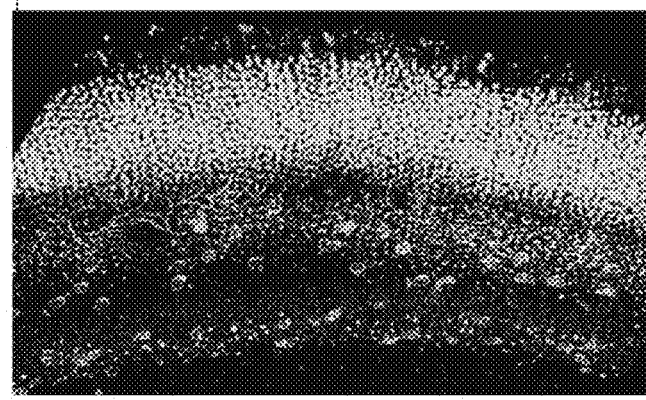

From these "double positive" cells, the AAV were isolated and sequenced. Five (5) variants were sequenced (FIG. 5). AAV vectors were then created using each of these mutant sequences in place of the wild type AAV8 capsid gene in an AAV(EF1α-EGFP) vector. This virus expresses EGFP under the control of human EF1α promoter (Nakai et al, J. Virology, 79(6):3606-14 (March 2005), which is hereby incorporated by reference). One additional mutant, carrying a premature stop codon, was also used to create a virus (Variant 5, FIG. 5). These viruses were subretinally injected (1.5 µl) into 10 week old C57Bl6 (WT) mice. After three weeks the mice were sacrificed, the retinas removed and 150 µm vibratome sections were made of the tissue (see, e.g., http://www.immunostar.com/content/pdf/instruction_manual.pdf) FIGS. 6A-E show expression of EGFP in retina injected with AAV variants 1-5. Variant 1 shows fluorescence in a diverse range of cell types with the sparsest fluorescence between the outer (OPL) and inner (IPL) plexiform layers where the bipolar cell subtypes are found (FIG. 6A). This layering is identified using a marker for choline acetyl transferase (anti-ChAT). The transduction pattern for variant 1 is qualitatively similar to that seen with the wild-type AAV8 capsid. By contrast strong fluorescence staining is found for variant 2 (AAV8b) in this outer-inner plexiform region (FIG. 6B, shown by an arrow) with many bipolar and amacrine cells stained. Bipolar cell staining is identified here with the marker anti-PKCα. In addition the photoreceptor cell bodies in the outer nuclear layer and their outer segments are strongly stained. The variant 3 virus shows a more distinctive staining pattern with dense staining along the outer plexiform layer with labeling of the horizontal cell bodies and their dense network of spreading dendrites (FIG. 6C, shown by an arrow). The lack of staining in the outer nuclear layer suggests that this variant selects against transduction of the photoreceptor cells. Variant 4 staining is sparse with only a few horizontal and amacrine cells labeled (FIG. 6D). Variant 5 carried a premature stop codon and effectively served as a negative control (FIG. 6E).

Variant 2, preferentially transduced bipolar cells and was termed AAV8-b. Variant 3 preferentially transduced horizontal cells and was termed AAV8-h. Based upon these results, variants 2 and 3 were selected for further analysis.

Example 3: Expression from AAV8-b Compared to AAV8wt Using the Ubiquitous Promoter EF1α

1.5 µl of AAV8-b(EF1α-EGFP) at a titer of $5.3 \times 10^{12}$ gc/ml was subretinally injected into 10 week old C57Bl6 (WT) mice (n=5). For comparison, 1.5 µl of AAV8 wt-(EF1α-EGFP) at a titer of $6.4 \times 10^{13}$ gc/ml was subretinally injected into 10 week old C57Bl6 (WT) mice (n=5). After three weeks the mice were sacrificed, the retinas removed and 150 µm vibratome sections were made of the tissue. Immunostaining was performed to identify bipolar cell strata (anti-ChAT). This requires a 7-day incubation causing a loss in fluorescence, therefore GFP was also labeled (anti-GFP). Sections were imaged by confocal microscopy with equivalent laser intensities, gains and step sizes for a 40× z-stack. Fluorescent bipolar cells are marked with an arrow to distinguish them from amacrine cells (FIG. 7). The amacrine cell bodies lie just beneath the bipolar cell bodies and have a dendritic tree spreading horizontally across the retinal plane directly from the cell body. The bipolar cell body has a 'true' axon descending through the inner plexiform layer to the terminal boutons at the ganglion cell layer (see also FIG. 11: AAV-8b-mG6-EGFP).

Fluorescence staining shows a strong transduction of the Bruch's membrane and the inner limiting membrane of mouse retina by AAV8 wt-EF1α.EGFP. In contrast, these membranes are not fluorescent in retinas transduced with AAV8b-EF1α.EGFP. This may account for the greater diffusion of the AAV8b virus through the retina with stronger fluorescence in the region between the inner and outer plexiform layers for AAV8b compared to AAV8wt. Note that these retinas were also labeled for acetyl choline transferase to identify the region between the inner and outer plexiform layers.

Figure 12A:
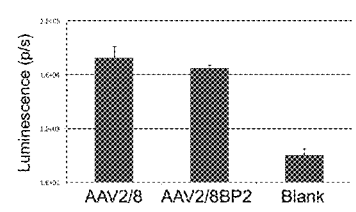
FIGS. 12A-12D show analysis of transduction properties of AAV8BP2. Titre analysis of the yield of purified AAV2/8BP2 compared to AAV2/8 (12a). Retinas from WT mice subretinally injected with AAV2/8 (EF1α-EGFP) or AAV2/8BP2(EF1α-EGFP) were collected three weeks post-injection and used for FACS analysis (n=4) (12b). QrtPCR to identify bipolar cell gene expression level was carried out on RNA from the GFP pool for each group (12c) and showed 120% increase in Grm6 expression (p=0.05) and 67% increase in trpM1L expression (p<0.05). Equivalent expression levels are determined for the cone photoreceptor genes Opn mwl and Opn swl (12d).
Figure 12B:
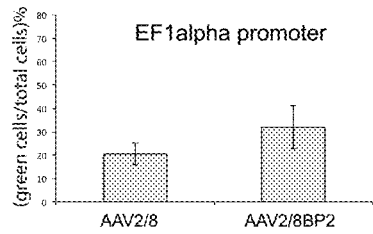
Figure 12C:
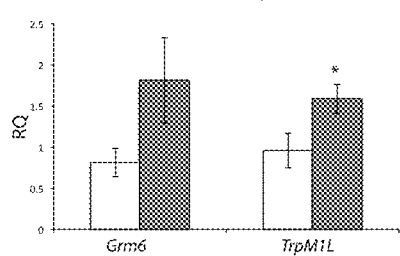
Figure 12D:
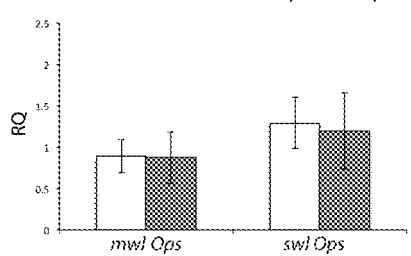

Example 4: Quantitative Analysis of AAV2/8BP2 in the Retina Using a Non-Cell-Specific Promoter In vitro and in vivo transduction of AAV2/8BP2 was assayed using pure large-scale preparation. BP2 was confirmed to transduce HEK293 cells in vitro similarly to the parental AAV2/8 suggesting that the modified epitope was not having a significant negative impact on viral packaging (FIG. 12a). Adult C57bl6 mice were subretinally injected with titre-matched AAVs expressing EGFP under the EF1α promoter and made using either the unmutated AAV8 capsid or the mutant AAV8BP2. After three weeks the retinas were dissociated and processed for FACS analysis. Cell counts (FIG. 12b) show 20% transduction of retinas injected with AAV2/8 versus 32% transduction of retina injected with AAV2/8BP2. A pool of 100,000 cells was taken from each sorted fraction and the relative expression of retinal genes in the green and non-green cell populations was tested by qRT-PCR. Increased expression from bipolar-cell-specific genes, Grm6 and the long form of a transient receptor potential cation channel, TrpM1L was found for the AAV2/8BP2-injected retinas. A 120% increase in Grm6 expression and 67% increase in TrpM1L expression were determined (FIG. 12c). By contrast, equivalent expression levels of cone opsin genes were measured between the pools for AAV2/8 versus AAV2/8BP2 retinas (FIG. 12d), suggesting targeting to the bipolar cells is being achieved even with a strong constitutive promoter such as EF1α.

Example 5: Transduction of Wild-Type Dog Retina with AAV8-b

Both eyes of a normal-sighted, approximately 14 month old male dog were injected with AAV8-b. The right eye received a subretinal injection of $1.66 \times 10^{10}$ genome copies (GC) in 0.2 ml. The left eye received an intravitreal injection of $1.66 \times 10^{10}$ in 0.2 ml. The dog was examined by ophthalmoscopy daily after injection to monitor for potential inflammation and to determine when transgene expression first became apparent. Thereafter the animal was evaluated at weekly intervals. Fundus photographs were made 22 days after injection. The animal was euthanized 33 days after injection. The ophthalmoscopic appearance had not changed from that noted on day 22.

Figure 8:
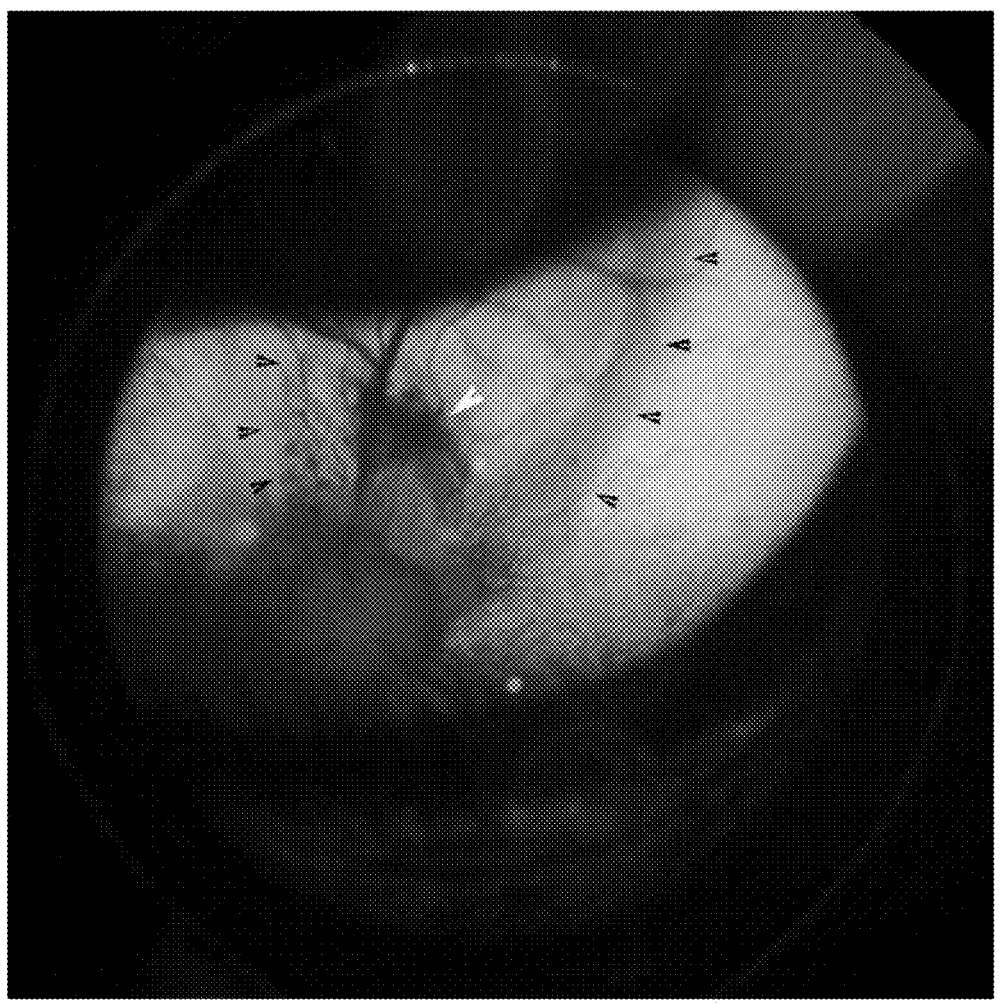
FIG. 8 is a fundus photograph of canine eye that had received subretinal injection of AAV8-b. Photo was taken 22 days after injection. The view shows the tapetal half of the retina. Black arrowheads demarcate the region of retina that is EGFP-positive due to exposure to the AAV8-b virus. The white arrowhead indicates the retinotomy site. The optic disc is at the bottom of the image.

No inflammation was noted at any timepoint following injection. EGFP was first identified by ophthalmoscopy 5 days after injection in the subretinally injected eye. Levels of EGFP detectable by ophthalmoscopy increased through the two week timepoint and plateaued (FIG. 8). No EGFP was detectable by ophthalmoscopy in the intravitreally injected eye. It was noted that the dog remained healthy and active throughout the study. At necropsy, no abnormalities were noted in gross pathology.

Figure 9A:
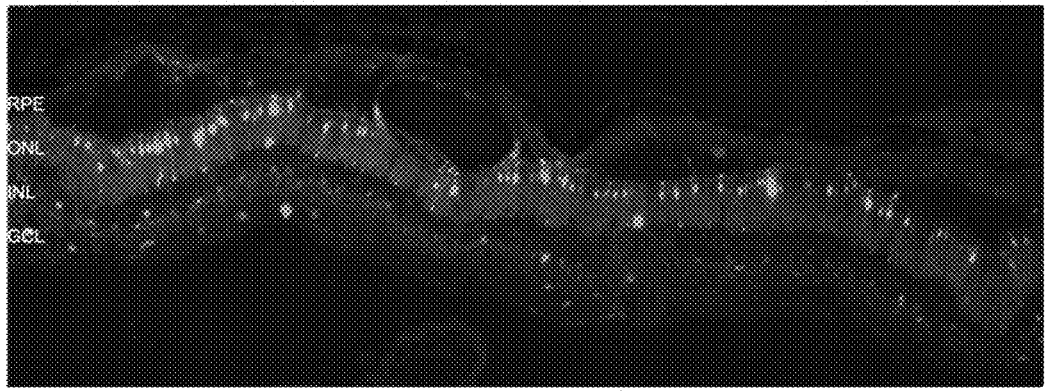
FIGS. 9A and B are photographs showing a section of canine retina from the GFP-positive region shown in FIG. 8, viewed with fluorescence microscopy. Nuclei are counterstained with DAPI.
Figure 9B:
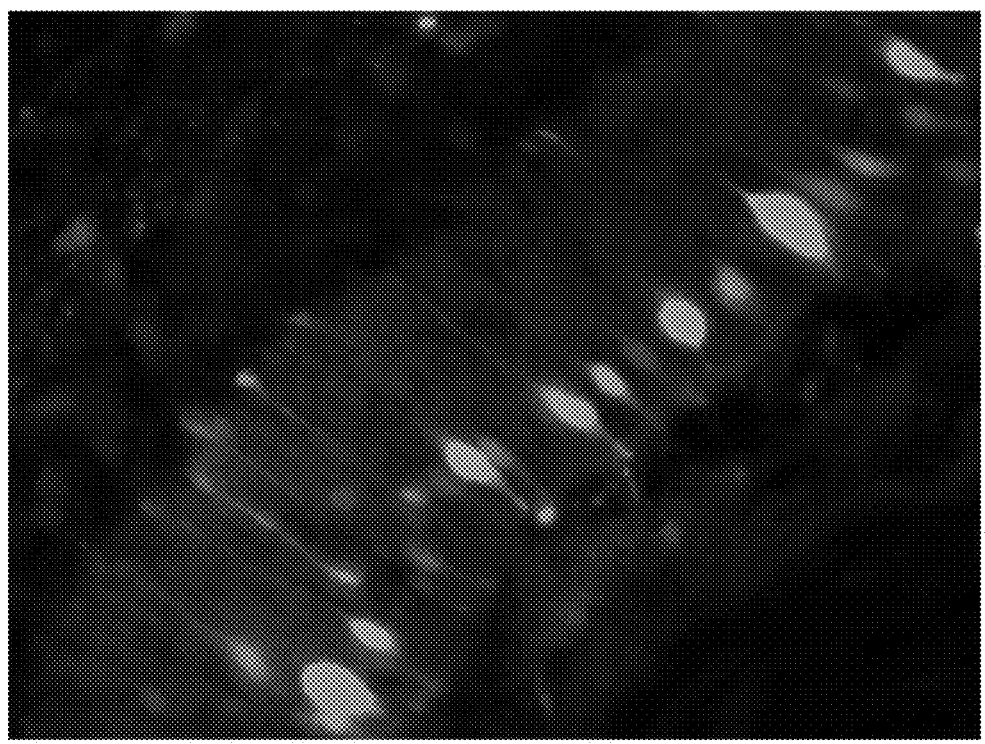
FIG. 9B is a higher magnification view of image shown in FIG. 9A. Strongly GFP positive cone photoreceptors are apparent as well as a few GFP-positive rod photoreceptors. GFP-positive inner retinal cells are also apparent.
Figure 10:
FIG. 10 is a photograph showing a section through the intravitreally-injected retina in the region of the optic nerve, viewed with fluorescence microscopy. Nuclei are counterstained with DAPI. Strongly GFP-positive ganglion cell axons are appreciated entering and spanning the optic nerve head. The ONL has normal thickness, demonstrating that there are no retinal degenerative changes. There are no other GFP-positive cells in the retina with the potential exception of some RPE cells at the junction of the optic nerve. It is noted that this may be autofluorescence, and not fluorescence specific to GFP, however. Abbreviations, same as FIG. 9.

Histologic analyses of the subretinally injected eye revealed no evidence of inflammation (cell infiltrate, immune cells) (FIG. 9) or retinal degeneration (there was normal thickness of photoreceptor layers in injected and uninjected regions of the retina) (FIG. 9A). GFP-positive cells were noted only in the region of subretinal injection (and in the region that appeared GFP-positive by ophthalmoscopy) (FIG. 9A). GFP-positive cells were tentatively identified by their morphology and location in the retina and included cone photoreceptors (FIGS. 9A-9B), inner nuclear cells, and ganglion cells. The inner nuclear cells (FIG. 9) and ganglion cells (FIG. 10) included cells with high levels of EGFP and also cells with lower levels of GFP.

Histologic analyses of the intravitreally injected eye revealed no evidence of inflammation (cell infiltrate, immune cells)(FIG. 10) or retinal degeneration. EGFP was detectable in ganglion cells by fluorescence microscopy.

Example 6: Expression of Channelrhodopsin Using a Bipolar Cell-Specific Promoter To test for bipolar cell-specific expression of an ocular protein, WT mice were injected subretinally with AAV8-b carrying ON-bipolar cell-specific promoter driving channelrhodopsin (ChR2)-EGFP. The ON-bipolar cell-specific promoter was the metabotropic glutamate receptor 6 (mGluR6) promoter. The OFF-bipolar cells terminate in sublamina 1 and 2 and have shorter axons than the ON-type which terminates in sublamina 4 and 5 (FIG. 11b). Thus, the ON-bipolar cell subtype can be distinguished from the OFF-bipolar cell using the ChAT staining which identifies the specific sublamina of the inner plexiform layer.

Figure 11A:
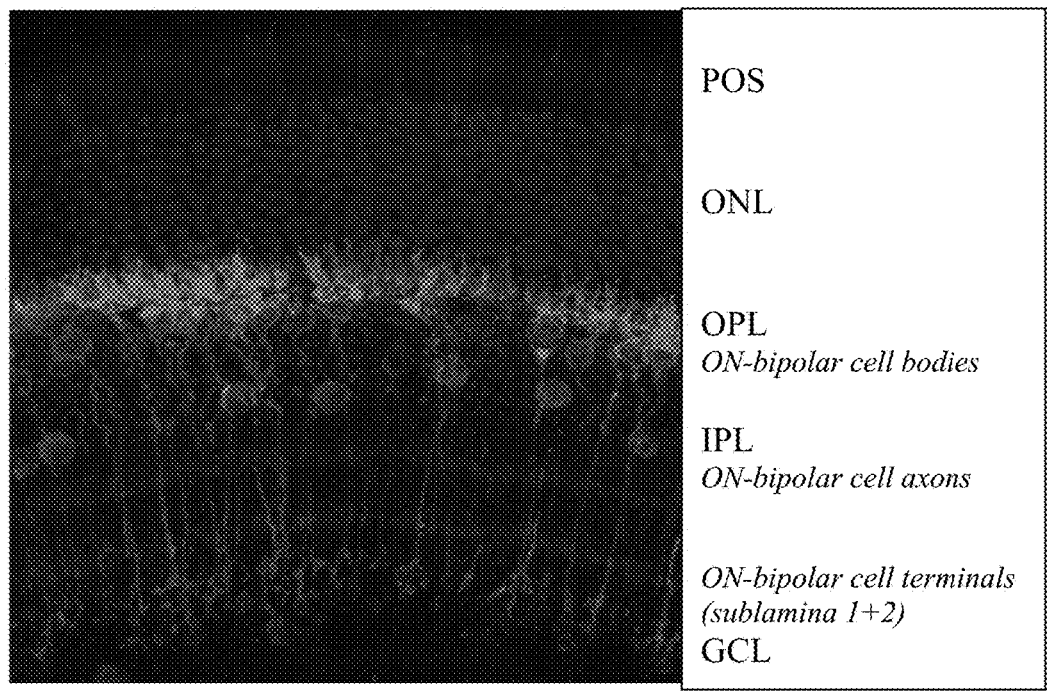
FIG. 11A is a photograph of a retinal section of a WT mouse injected subretinally with AAV8-b-mGluR6-ChR2-EGFP. The ON-bipolar cell subtype is distinguished from the OFF-bipolar cell using the ChAT staining which identifies the specific sublamina of the inner plexiform layer. The OFF-bipolar cells terminate in sublamina 1 and 2 and have shorter axons than the ON-type which terminates in sublamina 4 and 5. POS=Photoreceptor outer segments, ONL=Outer nuclear layer, OPL=outer plexiform layer, IPL=inner plexiform layer, GCL=Ganglion cell layer.
Figure 11B:
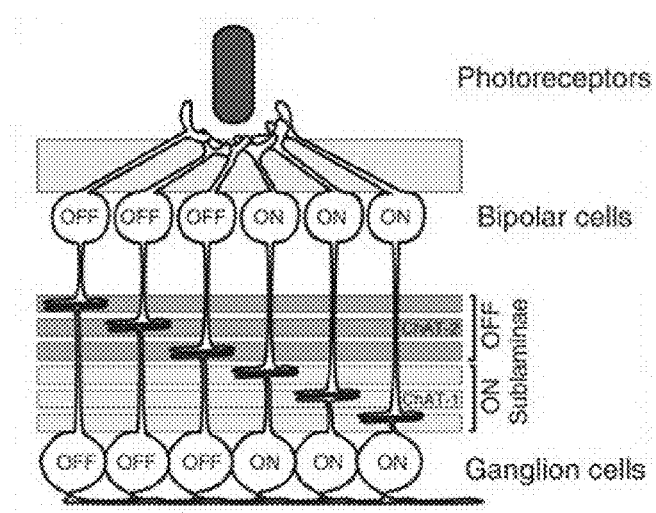
FIG. 11B is a diagram showing the structure of the inner retina including the biopolar cells and sublamina of the inner plexiform layer.

Expression in rod (ON) bipolar cells was observed (FIG. 11a). ON-bipolar cell terminals are bright (FIG. 11a), in the optimal location for ChR2 channels.

All publications, patents, and patent applications cited in this application, including U.S. Provisional Patent Application No. 61/762,775 are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims. Applicant hereby incorporates by reference the Sequence Listing material filed in electronic form herewith. This file is labeled "Z6471PCT_SequenceListing_ST25".

REFERENCES

1. Stieger, K., Cronin, T., Bennett, J. & Rolling, F. Adeno-associated virus mediated gene therapy for retinal degenerative diseases. Methods Mol Biol 807, 179-218 (2011).
2. Maguire, A. M., et al. Safety and efficacy of gene transfer for Leber's congenital amaurosis. N Engl J Med 358, 2240-2248 (2008).
3. Bainbridge, J. W., et al. Effect of gene therapy on visual function in Leber's congenital amaurosis. N Engl J Med 358, 2231-2239 (2008).
4. Hauswirth, W. W., et al. Treatment of leber congenital amaurosis due to RPE65 mutations by ocular subretinal injection of adeno-associated virus gene vector: short-term results of a phase I trial. Hum Gene Ther 19, 979-990 (2008).
5. Doroudchi, M. M., et al. Virally delivered Channelrhodopsin-2 Safely and Effectively Restores Visual Function in Multiple Mouse Models of Blindness. Mol Ther 19, 1220-1229 (2011).
6. Lagali, P. S., et al. Light-activated channels targeted to ON bipolar cells restore visual function in retinal degeneration. Nat Neurosci 11, 667-675 (2008).
7. Petrs-Silva, H., et al. Novel properties of tyrosine-mutant AAV2 vectors in the mouse retina. Mol Ther 19, 293-301 (2011).
8. Humayun, M., et al. Results Update from Second Sight's Argus II Retinal Prosthesis Study. in ARVO (Ft. Lauderdale, 2012).
9. Schwartz, S. D., et al. Embryonic stem cell trials for macular degeneration: a preliminary report. Lancet 379, 713-720 (2012).

What is claimed is:

1. A method of preventing, arresting progression of, or ameliorating vision loss associated with an ocular disorder in a subject, said method comprising administering to said subject an effective concentration of a composition comprising a recombinant adeno-associated virus (AAV) having a recombinant AAV capsid comprising a mutation in aa 587-595 of the AAV8 capsid protein sequence as compared to the AAV8 wild type capsid sequence or a mutation in a corresponding region of another AAV capsid protein as compared to the corresponding wild type capsid sequence, further comprising a minigene comprising AAV inverted terminal repeats and a heterologous nucleic acid sequence operably linked to regulatory sequences which direct expression of a product encoded by the heterologous nucleic acid sequence in a target cell, and a pharmaceutically acceptable carrier, wherein the AAV capsid comprises the sequence of SEQ ID NO: 1 or SEQ ID NO: 2.

2. The method according to claim 1, wherein the product encoded by the heterologous nucleic acid sequence is an opsin selected from rhodopsin, photopsin, L/M wavelength opsin (red/green)-opsin, short wavelength (S) opsin (blue), channelrhodopsin and halorhodopsin; NYX, GRM6, TRPM1L or GPR179.

3. The method according to claim 1, wherein the composition is administered by subretinal injection.

4. The method according to claim 1, wherein the subject has, or is at risk of developing, retinitis pigmentosa, rod-cone dystrophy, Leber's congenital amaurosis, Usher's syndrome, Bardet-Biedl Syndrome, Best disease, retinoschisis, Stargardt disease (autosomal dominant or autosomal recessive), untreated retinal detachment, pattern dystrophy, cone-rod dystrophy, achromatopsia, ocular albinism, enhanced S cone syndrome, diabetic retinopathy, age-related macular degeneration, retinopathy of prematurity, sickle cell retinopathy, Congenital Stationary Night Blindness, retinal vein occlusion, glaucoma, Leber's hereditary optic neuropathy, lysosomal storage disorder, peroxisomal disorder.

5. The method according to claim 1, wherein the effective concentration is about $10^9$ to $10^{13}$ genome copies per milliliter (GC/mL).

6. The method according to claim 1, wherein the AAV is a self-complementary AAV.

7. A method of targeting bipolar cells for optogenetic therapy in a subject in need thereof, the method comprising administering to said subject an effective concentration of a composition comprising a recombinant adeno-associated virus (AAV) having a recombinant AAV capsid comprising a mutation in aa 587-595 of the AAV8 capsid protein sequence as compared to the AAV8 wild type capsid sequence or a mutation in a corresponding region of another AAV capsid protein as compared to the corresponding wild type capsid sequence, further comprising a minigene comprising AAV inverted terminal repeats and a heterologous nucleic acid sequence operably linked to regulatory sequences which direct expression of a product encoded by the heterologous nucleic acid sequence in a target cell, and a pharmaceutically acceptable carrier, wherein the AAV capsid comprises the sequence of SEQ ID NO: 1 or SEQ ID NO: 2.

8. A method of generating a recombinant adeno-associated virus (rAAV) comprising an AAV capsid comprising culturing a host cell containing: (a) a molecule encoding a recombinant AAV capsid protein characterized by a mutation in aa 587-595 as compared to the wild type AAV8 vp1 capsid sequence, or a mutation in the analogous region of another AAV capsid as compared to the corresponding AAV wild type capsid sequence, wherein the AAV capsid comprises the sequence of SEQ ID NO: 1 or SEQ ID NO: 2; (b) a functional rep gene; (c) a minigene comprising AAV inverted terminal repeats (ITRs) and a heterologous nucleic acid sequence operably linked to regulatory sequences which direct expression of a product encoded by the heterologous nucleic acid sequence in the target cell; and (d) sufficient helper functions to permit packaging of the minigene into the AAV capsid protein.

9. A method of delivering a transgene to a cell, said method comprising contacting the cell with an AAV having a recombinant AAV capsid comprising a mutation in aa 587-595 of the AAV8 capsid protein sequence as compared to the AAV8 wild type capsid sequence or a mutation in a corresponding region of another AAV capsid protein as compared to the corresponding wild type capsid sequence, further comprising a minigene comprising AAV inverted terminal repeats and a heterologous nucleic acid sequence operably linked to regulatory sequences which direct expression of a product encoded by the heterologous nucleic acid sequence in a target cell, wherein the AAV capsid comprises the sequence of SEQ ID NO: 1 or SEQ ID NO: 2 and a pharmaceutically acceptable carrier.

* * * * *